US006759574B1

(12) United States Patent
Ream, Jr. et al.

(10) Patent No.: US 6,759,574 B1
(45) Date of Patent: Jul. 6, 2004

(54) PLANTS HAVING ENHANCED GALL RESISTANCE AND METHODS AND COMPOSITIONS FOR PRODUCING SAME

(75) Inventors: Lloyd Walter Ream, Jr., Corvallis, OR (US); Machteld Mok, Corvallis, OR (US); Hyewon Lee, Pusan (KR)

(73) Assignee: The State of Oregon Acting by and through the State Board of Higher Education on Behalf of Oregon State University, Corvallis, OR (US)

( * ) Notice: Subject to any disclaimer, the term of this patent is extended or adjusted under 35 U.S.C. 154(b) by 0 days.

(21) Appl. No.: 09/434,837

(22) Filed: Nov. 4, 1999

Related U.S. Application Data

(60) Provisional application No. 60/107,185, filed on Nov. 5, 1998.

(51) Int. Cl.[7] .............................. A01H 5/00; A01H 1/00; C12N 15/11; C12N 15/31; C12N 15/87
(52) U.S. Cl. ........................ 800/301; 800/278; 800/279; 800/260; 800/298; 536/23.1; 435/468
(58) Field of Search ................................. 800/301, 260, 800/298, 278, 279, 285, 319, 323.2; 536/23.1; 435/419, 468

(56) References Cited

U.S. PATENT DOCUMENTS

| | | | |
|---|---|---|---|
| 5,034,323 A | | 7/1991 | Jorgensen et al. |
| 5,217,889 A | | 6/1993 | Roninson et al. |
| 5,567,599 A | * | 10/1996 | Lemieux ................. 435/172.3 |
| 5,583,021 A | | 12/1996 | Dougherty et al. |
| 5,681,730 A | * | 10/1997 | Ellis ....................... 435/172.3 |
| 5,686,649 A | | 11/1997 | Chua et al. |
| 5,792,927 A | * | 8/1998 | Firoozabady et al. ....... 800/205 |
| 5,929,306 A | | 7/1999 | Torisky et al. |
| 6,268,552 B1 | | 7/2001 | Li |
| 6,506,559 B1 | | 1/2003 | Fire et al. |

FOREIGN PATENT DOCUMENTS

| | | |
|---|---|---|
| EP | 0223 399 | 10/1986 |
| JP | 05068574 A | 5/1991 |
| JP | 68574 | 3/1993 |
| WO | WO93/17098 | 9/1993 |
| WO | WO98/49888 | * 11/1998 |
| WO | WO99/20777 | 4/1999 |
| WO | WO 99/53050 | 10/1999 |

OTHER PUBLICATIONS

Hartman et al, 1983, Plant Propagation 4th edition, pp. 355–349 and 351–358.*
James et al, "Genetic transformation of apple (Malus pumila Mill.) using a disarmed Ti–binary vector", 1989, Plant Cell Reports vol. 7, pp. 658–661.*
Moonan et al., "Analyses of Genotypic Diversity . . . Intraspecific Spatial Phylogenetic Variation", 2002, Journal of Virology vol. 76, No. 3 pp. 1339–1348.*

Baulcombe, "Unwinding RNA Silencing," *Science*, vol. 290, pp. 1108–1109, Nov. 10, 2000.
Fire et al., "Potent and specific genetic interference by double–stranded RNA in *Caenorhabitis elegans*," *Nature*, vol. 391, pp. 806–811, Feb. 19, 1998.
Montgomery et al., "Double–stranded RNA as a mediator in sequence–specific genetic silencing and co–suppression," *TIG*, vol. 14, No. 7, pp. 255–258, Jul. 1998.
Montgomery et al., "RNA as a target of double–stranded RNA–mediated genetic interference in *Caenorhabditis elegans*," *Proc. Natl. Acad. Sci. USA*, vol. 95, pp. 15502–15507, Dec. 1998.
Sharp et al., "RNA Interference," *Science*, vol. 287, pp. 2431–2432, Mar. 31, 2001.
Timmons et al., "Specific interference by ingested dsRNA," *Nature*, vol. 395, p. 854, Oct. 29, 1998.
Smith et al., *Nature* 334:724–726, 1988.
Bird et al., *Biotechnology and Genetic Engineering Reviews* 9:207–227, 1991.
Wassenegger et al., "A Model for RNA–Mediated Gene Silencing in Higher Plants," *Plant Molecular Biology* 37:349–362, 1998.
Ream et al., "Multiple Mutations in the T Region of the Agrobacterium Tumefaciens Tumor–Inducing Plasmid," *Proc. Natl. Acad. Sci. USA* 80:1660–1664, Mar., 1993.
Marsh et al., "Artificial Defective Interfering RNAs Derived From Brome Mosaic Virus," *J. Gen Virol.* 72:1787–1792, 1991.
Voinnet et al., "Systemic Signalling in Gene Silencing," *Nature* 389:553, Oct., 1997.
Tabara et al., "RNAi in C. Elegans: Soaking in the Genome Sequence," *Science* 282:42–43, Oct. 16, 1998.
Marano et al., "Pathogen–Derived Resistance Targeted Against the Negative–Strand RNA of Tobacco Mosaic Virus: RNA Strand–Specific Gene Silencing?," *The Plant Journal* 13(4):537–546, 1998.
Palauqui et al., "Systemic Acquired Silencing: Transgene–Specific Post–Transcriptional Silencing is Transmitted By Grafting From Silenced Stocks to Non–Silenced Scions," *The EMBO Journal* 16:4738–4745, 1997.
Lindbo et al., "Pathogen–Derived Resistance to a Potyvirus: Immune and Resistant Phenotypes in Transgenic Tobacco Expressing Altered Forms of a Potyvirus Coat Protein Nucleotide Sequence," *Molecular Plant–Microbe Interactions* 5:144–153, 1992.

(List continued on next page.)

Primary Examiner—Elizabeth F. McElwain
Assistant Examiner—Stuart F. Baum
(74) Attorney, Agent, or Firm—Klarquist Sparkman, LLP

(57) ABSTRACT

Methods and compositions for suppressing gall formation in plant cells induced by Agrobacterium infection are disclosed. The methods involve introducing at least one DNA construct, encoding at least one untranslatable sense-strand RNA and/or double-stranded RNA, into a plant cell. Introduction of these molecules into the plant cell causes the plant cells to become resistant to gall formation.

23 Claims, 5 Drawing Sheets

OTHER PUBLICATIONS

Dougherty et al., "RNA–Mediated Virus Resistance in Transgenic Plants: Exploitation of a Cellular Pathway Possibly Involved in RNA Degradation," *Molecular Plant–Microbe Interactions (MPMI)* 7:544–552, 1994.

Lindbo et al., "Untranslatable Transcripts of the Tobacco Etch Virus Coat Protein Gene Sequence Can Interfere with Tobocco Etch Virus Replication in Transgenic Plants and Protoplasts," *Virology* 189:725–733, 1992.

Smith et al., "Transgenic Plant Virus Resistance Mediated by Untranslatable Sense RNAs: Expression, Regulation, and Fate of Nonessential RNAs," *The Plant Cell* 6:1441–1453, Oct. 1994.

Palauqui et al., "Transgenes Are Dispensable for the RNA Degradation Step of Cosuppression," *Proc. Natl. Acad. Sci. USA* 95:9675–9680, Aug., 1998.

Iglesias et al., "Molecular and Cytogenetic Analyses of Stably and Unstably Expressed Transgene Loci in Tobacco," *The Plant Cell* 9:1251–1264, Aug. 1997.

Ruiz et al., "Initiation and Maintenance of Virus–Induced Gene Silencing," *The Plant Cell* 10:937–946, Jun., 1998.

Kawchuk et al., "Sense and Antisense RNA–Mediated Resistance to Potato Leafroll Virus in Russet Burbank Potato Plants," *Mol. Plant Microbe Inter.* 4(3):247–253, 1991.

van der Wilk et al., "Expression of the Potato Leafroll Luteovirus Coat Protein Gene in Transgenic Potato Plants Inhibits Viral Infection," *Plant Mol. Biol.* 17:431–430, 1991.

Powell et al., "Protection Against Tobacco Mosaic Virus Infection in Transgenic Plants Requires Accumulation of Coat Protein Rather Than Coat Protein RNA Sequences," *Virology* 175:124–130, 1990.

Xue et al., "Transformation of Five Grape Rootstocks With Plant Virus Genes and a virE2 Gene From *Agrobacterium tumefaciens*," *In Vitro Cell. Dev. Biol.* 35:226–231, May–Jun., 1999.

Clare et al., "Characteristics of the Nopaline Catabolic Plasmid in Agrobacterium Strains K84 and K1026 Used for Biological Control of Crown Gall Disease," *Plasmid* 23:126–137, 1990.

Sitbon et al., "Transgenic Tobacco Plants Coexpressing the *Agrobacterim tumefaciens*iaaM and iaaH Genes Display Altered Growth and Indoleacetic Acid Metabolism," *Plant Physiol.* 99:1062–1069, 1992.

Weiler et al., "Hormone Genes and Crown Gall Disease," *TIBS* 271–275, Jul., 1987.

Nam et al., "Differences in Susceptibility of Arbidopsis Ecotypes to Crown Gall Disease May Result From a Deficiency in T–DNA Integration," *The Plant Cell* 9:317–333, Mar. 1997.

Doughtery and Parks, "Transgenes and Gene Suppression Telling US Something New?" *Current Opinion in Cell Biology*, 7:399–405, 1995.

* cited by examiner

PLANTS HAVING ENHANCED GALL RESISTANCE AND METHODS AND COMPOSITIONS FOR PRODUCING SAME

CROSS REFERENCE TO RELATED CASES

This application claims priority from a co-pending U.S. Provisional Application No. 60/107,185, filed Nov. 5, 1998, which is incorporated herein by reference.

GOVERNMENTAL SUPPORT

This invention was made with government support under grants numbered 96-34354-3072 and 2002-35319-11555, awarded by the United States Department of Agriculture. The federal government has certain rights in the invention.

FIELD OF THE INVENTION

This invention is directed generally to compositions and methods for producing plants resistant to gall disease. The methods involve transforming plants with nucleic acid constructs encoding sense-strand untranslatable RNA molecules and/or double-stranded RNA molecules, RNA molecules that are similar to (but not identical to) certain Agrobacterium tumor-inducing genes.

BACKGROUND OF THE INVENTION

Several different recombinant DNA technologies have been employed to interfere with gene expression in plants including technologies based on ribozyme molecules, antisense RNA molecules, and co-suppression constructs. For a general discussion of ribozyme technology, antisense technology and co-suppression technology, see Castanotto, *Crit. Rev. Eukaryot Gen. Expr.* 2:331–357,1997; Simons, *Gene,* 72:35–44, 1988; and Jorgensen, *Biotechnol.* 8:340–344, 1990, respectively.

In addition to standard co-suppression techniques, researchers have studied the suppression of a target gene caused by the introduction of an untranslatable sense-strand transgene. (Dougherty and Parks, *Curr. Opin. Cell Biol.* 7:399–405, 1995; Jorgensen et al., *Science,* 279:1486–1487, 1998). This method has been used to silence a number of endogenous plant genes, as well as viral genes. (Marano and Baulcombe, *Plant J.* 13:537–546, 1998; Conner et al., *Plant J.* 11:809–823, 1997, Dougherty et al., *Mol. Plant-Microbe Interact.* 7:544–552, 1994; and Smith et al., *Plant Cell* 6:1441–1453, 1994).

The bacterial genus Agrobacterium contains several species that cause disease in economically important plants. For example, *Agrobacterium tumefaciens* causes gall tumors when it infects the wounded tissue of certain dicotyledonous plants such as apple trees and grape vines (DeCleene and DeLey, *Bot. Rev.* 42:389–466, 1976). Pathogenic strains of Agrobacterium harbor a tumor-inducing (Ti) plasmid that carries genes essential for gall tumorigenesis (Watson et al., *J. Bacteriol.* 123:255–264, 1975; Van Larebeke et al., *Nature* 252:169–170, 1974). The transferred DNA ("T-DNA"; FIG. 1) portion of the Ti plasmid enters the cells of susceptible plants and integrates into nuclear DNA (Chilton et al., *Cell* 11:263–271, 1977; Willmitzer et al., *Nature* 287:359–361, 1980; Chilton et al., *Proc. Natl. Acad Sci. USA* 77:4060–4064, 1980). Following T-DNA integration in cellular DNA, expression of three T-DNA genes, iaaM, iaaH, and ipt, leads to overproduction of the plant growth hormones auxin and cytokinin, resulting in tumorous growths referred to as "galls." (Ream, *Annual Rev. Phytopathol.* 27:583–618, 1989; Winans, *Micro. Revs.* 56:12–31, 1992; and Zambryski, *Annu. Rev. Plant Physiol. Plant Mol. Bio.* 43:465–490, 1992) (FIG. 2). The iaaM, iaaH, and ipt genes have been well characterized, and the sequences of these genes are available for example in the Genbank database under accession numbers X56185, M25805, and X17428, respectively.

iaaM and iaaH are required for auxin production: the enzyme encoded by iaaM converts tryptophan into indole acetamide, which the enzyme encoded by iaaH converts into indole acetic acid, an auxin (Schroeder et al., *Eur. J. Biochem.* 138:387–391, 1984; Thomashow et al., *Proc. Natl. Acad. Sci.* 81:5071–5075, 1985; Thomashow et al., *Science* 231:616–618, 1986; and Inze et al., *Mol. Gen. Genet.* 194:265–274, 1984). Loss of either enzyme prevents auxin production. ipt is required for cytokinin production; the enzyme encoded by this gene converts adenosine monophosphate into isopentenyl adenosine monophosphate, a cytokinin (Akiyoshi et al. *Proc. Nall. Acad Sci. USA* 81:5994–5998, 1984; Barry et al., *Proc. Natl. Acad. Sci. USA* 81:4776–4780, 1984; and Buchmann et al., *EMBO J.* 4:853–859, 1985). Inactivation of ipt and either one of the two auxin-biosynthesis genes on the Ti plasmid will reduce gall formation (Ream et al., *Proc. Natl. Acad. Sci. USA* 80:1660–1664, 1983).

Additionally, galls can be formed in cases in which just the cytokinin pathway, or only the auxin biosynthesis pathway, is functional. In these cases the galls are visually distinguishable based on their different morphological characteristics. For example, plants infected with an Agrobacterium strain that carries only the gene necessary for the production of auxin develop necrotic galls. In contrast, plants infected with strains of the bacteria that induce only the production of cytokinin produce shooty galls.

To date, adequate means do not exist to control gall disease on grape vines, fruit trees, nut trees, chrysanthemums, roses, cane berries, ornamental shrubs, and other nursery crops. Inoculation of plants with *Agrobacterium radiobacter* strain K84 affords some protection against specific strains of *A. tumefaciens* (Moore, *MicrobioL Sci* 5:92–95, 1988); however, gall disease remains a multimillion dollar worldwide problem. *Arabidopsis thaliana* plants resistant to gall disease have been produced by a traditional genetic approach (Nam et al., *Plant Cell* 9:317–333, 1997), but this strategy currently is not applicable to plants in which gall is a problem.

This invention is directed towards a new, more effective method of producing plants that are substantially resistant to gall disease caused by bacteria.

SUMMARY OF THE INVENTION

The present invention provides compositions that can be used to prevent tumor (gall) formation in plants infected with bacterial pathogens such as *Agrobacterium tumefaciens* and other species of Agrobacterium. These compositions comprise nucleic acid molecules that, when introduced into plants, can produce transgenic plants having enhanced resistance to tumors caused by such pathogens. The invention also encompasses transgenic plants that contain these nucleic acid molecules.

In general terms, the invention involves the use of nucleic acid constructs that encode untranslatable single-stranded RNA, double-stranded RNA, and/or untranslatable double-stranded RNA molecules that share specified high levels of sequence identity with target genes in the bacterial pathogen. For example, the constructs may encode one or more types of untranslatable RNA molecules sharing high levels of sequence identity with one or more of the iaaM, iaah, or ipt tumor genes of Agrobacterium. The invention also provides nucleic acid constructs that encode multiple different untranslatable single-stranded RNA, double-stranded RNA, and/or untranslatable double-stranded RNA molecules, including both sense and antisense RNA molecules. For example, one construct provided by the invention encodes untranslatable RNA forms of both the ipt and iaaM genes of *Agrobacterium tumefaciens*; this construct can suppress both shooty and necrotic gall formation in plants caused by a pathogenic strain of *A. tumefaciens* infecting the iplant.

The untranslatable RNA molecules appear to inhibit gall formation by triggering sequence-specific destruction of RNA molecules encoded by certain "target genes" of the infecting pathogen in the plant. However, the mechanism by which this occurs is not fully understood. For optimal efficacy, the untranslatable single-stranded RNA, double-stranded RNA, and/or untranslatable double-stranded RNA molecules should be of a sufficient length and share a minimum degree of sequence identity with the target bacterial gene such that disease resistance is conferred to the host cell. The level of disease resistance conferred to the host cell by the RNA molecule can be determined using the experiments described below. Thus, the RNA molecules encoded by the constructs provided herein are typically at least 25 nucleotides in length and share at least 60% sequence identity with the target gene of the pathogen. However, enhanced tumor suppression may be obtained by increasing the length of the untranslatable single-stranded RNA, double-stranded RNA, and/or untranslatable double-stranded RNA molecules (e.g., to at least 100, or at least 200 nucleotides) and/or by enhancing the level of sequence identity with the target gene (e.g., to at least 70%, 75%, 80%, or 90% sequence identity).

The invention also provides transgenic plants containing one or more of the above-described nucleic acid constructs. These constructs may be introduced into any plant species, but commercial crop plants for which Agrobacterium is a significant pathogen are expected to be particularly benefited by this technology.

The invention also provides chimeric plants that include both untransformed cells and transformed cells. These plants display "conferred resistance" in that the transgenic portion confers disease resistance to the non-transgenic portion. The chimeric plants are particularly useful for generating resistant, but not transgenic, fruits and other consumable portions of plants that are not transgenic.

SEQUENCE LISTINGS

The nucleic and amino acid sequences listed in the accompanying sequence listing are shown using standard letter abbreviations for nucleotide bases, and three-letter code for amino acids. Only one strand of each nucleic acid sequence is shown, but the complementary strand is understood as included by any reference to the displayed strand.

SEQ ID NO: 1 is a primer used to produce the mutant iaaM gene.

SEQ ID NO: 2 is a primer used to produce the mutant iaaM gene.

SEQ ID NO: 3 is a primer used to produce the mutant ipt gene.

SEQ ID NO: 4 is a primer used to produce the mutant ipt gene.

SEQ ID NO: 5 is the DNA sequence that encodes an untranslatable RNA molecule having a high sequence identity withthe *Agrobacterium ipt* gene.

SEQ ID NO: 6 is an amino acid sequence that is encoded by the untranslatable RNA molecule depicted in SEQ ID NO: 5.

SEQ ID NO: 7 is a DNA sequence encoding the untranslatable RNA molecule having a high sequence identity with the *Agrobacterium iaaM* gene.

SEQ ID NO: 8 is an amino acid sequence encoded by the untranslatable RNA molecule depicted in SEQ ID NO: 7.

SEQ ID NO: 9 is the nucleic acid sequence of the ipt/iaaM untranslatable construct.

SEQ ID NO: 10 is the nucleic acid sequence of the iaaM gene.

SEQ ID NO: 11 is the nucleic acid sequence of the iaaH gene.

SEQ ID NO: 12 is the nucleic acid sequence of the ipt gene.

DESCRIPTION OF DRAWINGS

FIG. 5(A) shows a BR construct in which one promoter (designated $P_1$) is used to express (direction of expression is indicated by the arrows) a DNA sequence encoding the sense-strand of a sequence that targets the ipt gene and the sense-strand of a sequence targeting the iaaM gene. This same construct also contains a second promoter (designated $P_2$) that drives the expression of the antisense-strand of the iaaM gene and the antisense-strand of the ipt gene. Thus, the combination of both promoters will generate a double-stranded RNA that contains a section targeting the ipt gene and a section targeting the iaaM gene. FIG. 5(B) shows a BR construct that contains one promoter ($P_1$) that expresses a DNA sequence encoding several different untranslatable RNA sequences that target both the ipt gene and the iaaM gene. Starting at the 5' end of the construct, the promoter $P_1$ drives the expression of a sense-strand targeting the ipt gene, a sense-strand targeting the iaaM gene, an antisense-strand targeting the iaaM gene, and a sense-strand targeting the ipt gene. This sequence can fold back on itself, and thus generate a double-stranded RNA molecule comprising regions homologous to both the ipt and iaaM gene. FIG. 5(C) shows another variation of a BR construct. This construct comprises independent promoters, $P_1$ and $P_2$, to drive the expression of an untranslatable RNA molecule in both the sense and anti-sense orientations, respectively. Two additional promoters ($P_3$ and $P_4$) are utilized for the expression of the sense and anti-sense expression of a second untranslatable RNA. FIG. 5(D) shows another variation of the BR construct. This construct comprises one promoter ($P_1$) to express first the sense-strand and then the antisense-strand of an untranslatable RNA molecule targeting the ipt gene. This construct also comprises a second promoter to express both the sense-strand and antisense-strand of an untranslatable RNA targeting the iaaM gene. FIGS. 5(E) and 5(F) illustrate additional variations that can be used to express single-stranded untranslatable RNA molecules.

DETAILED DESCRIPTION

1. Definitions and Abbreviations

Figure 1:
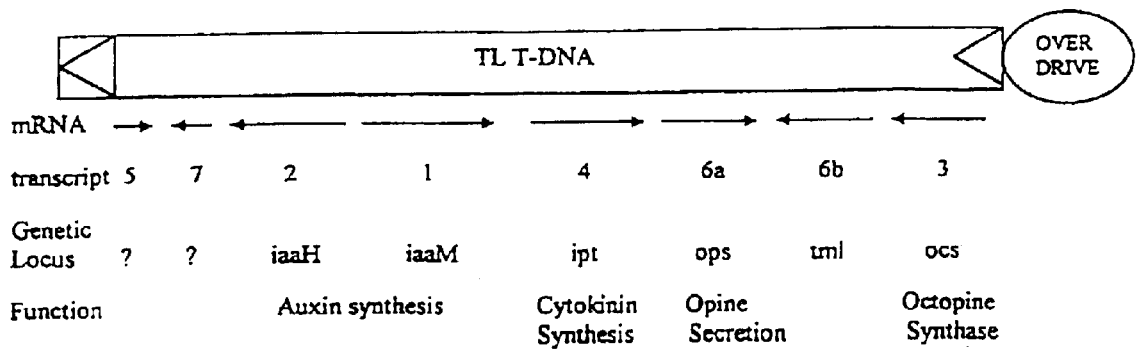
FIG. 1 is a diagram of the *A. tumefaciens* transferred DNA ("T-DNA") that contains three oncogenes: iaaM, iaaH, and ipt. Triangles represent T-DNA border sequences which delimit T-DNA ends by initiating and terminating T-DNA tnansfer (Peralta and Reaim *Proc. Natl. Acad. Sci.* 82:5112–5116, 1985). Arrows show direction and length of messenger RNAs (mRNAs) produced in gall tumors.
Figure 2:
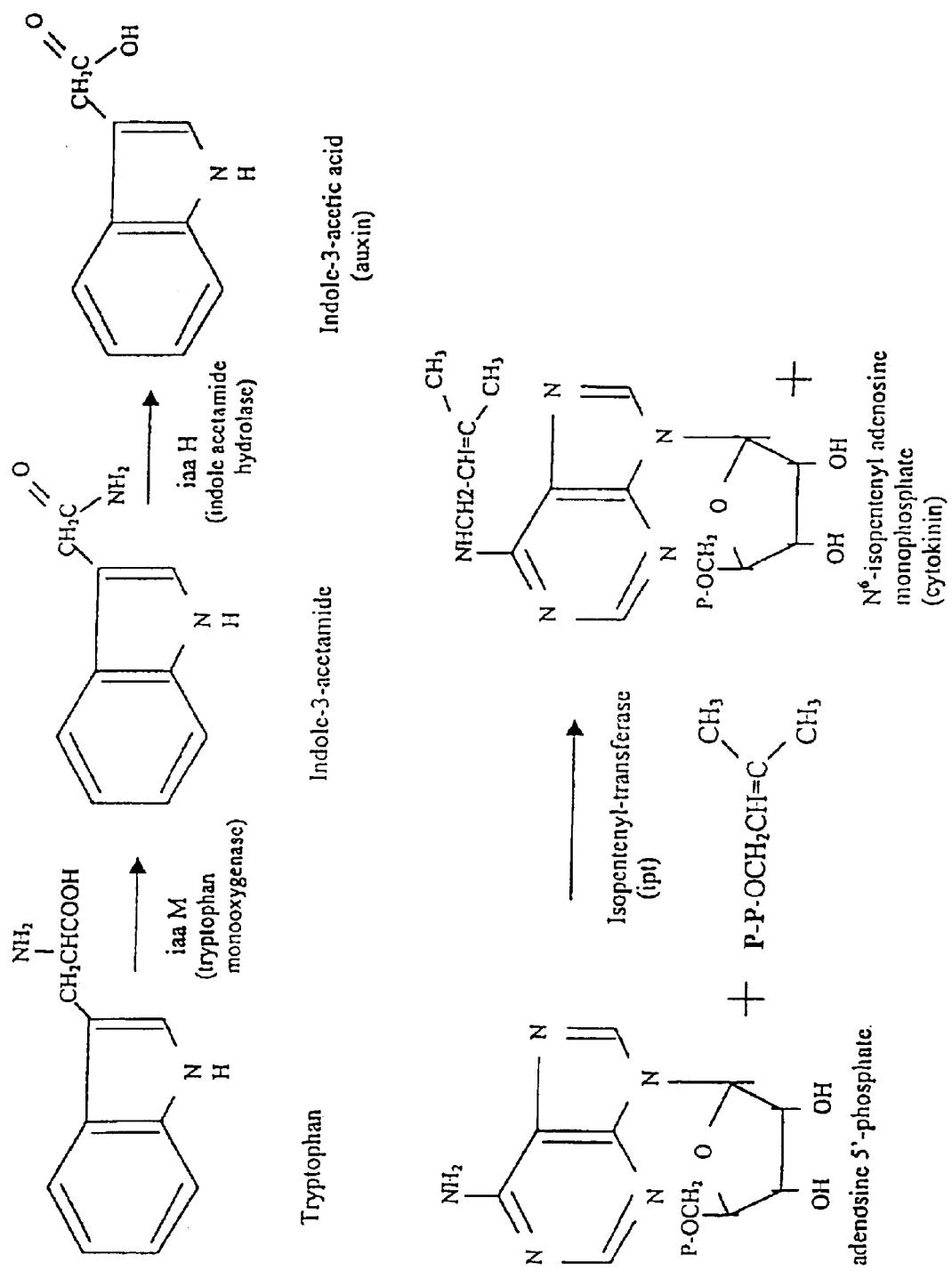
FIG. 2 is a diagram of the auxin and cytokinin biosynthetic pathways encoded by the *A. tumefaciens* T-DNA oncogenes.

Untranslatable RNA molecule: An RNA molecule, either single-stranded or double-stranded, that is based on a naturally occurring RNA molecule but which, as a result of genetic manipulation, is incapable of being translated to yield the full-lenght protein encoded by its naturally occurring counterpart. For example, such RNA can be rendered untranslatable through the introduction of one or more premature termination codons (TAA, TAG, or TGA), or by introduction of a mutation that shifts the reading frame. Alternatively, for example, the RNA may be rendered untranslatable by the deletion of the AUG translation-initiation codon, or of the AAUAAA polyadenylation signal. The RNA may also be rendered untranslatable by simply removing a portion of the CDNA encoding the full-length protein. Thus, even if the sequence were translated, it would produce a truncated version of its naturally occurring counterpart.

Antisense-strand RNA: An RNA molecule that is complementary to a messenger RNA (which represents a corresponding "sense" strand).

Disease-resistant transgenic plant: A "disease-resistant transgenic plant" as used herein is a transgenic plant exhibiting more resistance to gall disease than a corresponding non-transgenic plant.

Operably linked: A first nucleic acid sequence is operably linked with a second nucleic acid sequence whenever the first nucleic acid sequence is placed in a fumctional relationship with the second nucleic acid sequence. For instance, a promoter is operably linked to a coding sequence if the promoter affects the transcription or expression of the coding sequence. Generally, operably linked DNA sequences are contiguous.

Recombinant: A recombinant nucleic acid is one having a sequence that is not naturally occurring in the organism in which it is expressed, or has a sequence made by an artificial combination of two otherwise-separated, shorter sequences. This artificial combination is often accomplished by chemical synthesis or, more commonly, by the artificial manipulation of isolated segments of nucleic acids, e.g., by genetic engineering techniques. "Recombinant" is also used to describe nucleic acid molecules that have been artificially manipulated, but that contain the same control sequences and coding regions that are found in the organism from which the gene was isolated.

Sense-strand RNA: An RNA molecule that can serve directly as messenger RNA, i.e., that can be translated by ribosomes.

Double-stranded RNA: A "double-stranded RNA" is an RNA molecule that contains at least a 25-bp sequence including both a sense-strand and an antisense-strand. Double-stranded RNA molecules are additionally characterized by the level of complementarity between the sense-strand and the antisense-strand. Complementarity refers to the amount of base pairing between the two sequences. For example, the sequence 5'-AUCGGAUAGU-3' is 100% complementary to the sequence 5'-ACUAUCCGAU-3' and 70% complementary to the sequence 5'-GAAAUCCGAU-3'. The double-stranded RNA should be of a sufficient length and have a sufficient level of complementarity such that it confers disease resistance to the host cell (disease resistance can be determined using the assays described below). For example, the double-stranded RNA may have as little as 60% complementarity. Generally, however, double-stranded RNA sequences will have at least 70%, 75%, 80%, or 90% complementarity.

Vector: A "vector" is a nucleic acid molecule as introduced into a host cell, thereby producing a transformed host cell. A vector may include nucleic acid sequences, such as an origin of replication, that permit the vector to replicate in a host cell. A vector may also include one or more screenable markers, selectable markers, or reporter genes and other genetic elements known in the art.

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences.

Methods for aligning sequences for comparison purposes are well known in the art. Various programs and alignment algorithms are described in: Smith & Waterman, *Adv. Appl. Math.* 2:482, 1981; Needleman & Wunsch, *J Mol. Biol.* 48:443, 1970; Pearson and Lipman, *Proc. Natl. Acad. Sci. USA* 85:2444–2448, 1988; Higgins and Sharp, *Gene* 73:237–244, 1988; Higgins and Sharp, *CABIOS* 5:151–153, 1989; Corpet et al., *Nucleic Acids Research* 16:10881–10890, 1988; Huang, et al., *Computer Applications in the Biosciences* 8:155–165, 1992; and Pearson et al., *Methods in Molecular Biology* 24:307–331, 1994. Altschul et al., *J Mol. Bio.,* 215:403–410, 1990, presents a detailed consideration of sequence alignment methods and homology calculations.

The NCBI Basic Local Alignment Search Tool (BLAST™, Altschul et al. *J. Mol. Biol.,* 215:403–410, 1990) is available from several sources, including the National Center for Biotechnology Information (NCBI, Bethesda, Md.) and on the Internet, for use in connection with the sequence-analysis programs blastp, blastn, blastx, tblastn and tblastx. BLAST™ can be accessed at http://www.ncbi.nlm.nih.gov/BLAST/. A description of how to determine sequence identity using this program is available at http://www.ncbi.nlm.nih.gov/BLAST/blast_help.html.

For comparisons of amino acid sequences of greater than about 30 amino acids, the "Blast 2 sequences" function in the BLAST™ program is employed using the default BLO- SUM62 matrix set to default parameters, (gap existence cost of 11, and a per-residue gap cost of 1). When aligning short peptides (fewer than about 30 amino acids), the alignment should be performed using the Blast 2 sequences function, employing the PAM30 matrix set to default parameters (open gap 9, extension gap 1 penalties). Proteins having even greater similarity to the reference sequences will show increasing percentage identities when assessed by this method, such as at least 45%, at least 50%, at least 60%, at least 70%, at least 75%, at least 80%, at least 85%, at least 90%, or at least 95% sequence identity.

A first nucleic acid is "substantially similar" to a second nucleic acid if, when optimally aligned (with appropriate nucleotide insertions or deletions) with the other nucleic acid (or its complementary strand), nucleotide sequence identity occurs in at least about 60%, 75%, 80%, 85%, 90% or 95% of the nucleotide bases (As used herein, "optimally aligned" sequences exhibit a maximal possible sequence identity). Sequence similarity can be determined by comparing the nucleotide sequences of two nucleic acids using the BLAST™ sequence analysis software (blastn) available from The National Center for Biotechnology Information. Such comparisons may be made using the software set to default settings (expect=10, filter=default, descriptions=500 pairwise, alignments=500, alignment view=standard, gap existence cost=11, per residue existence=1, per residue gap cost=0.85). Similarly, a first polypeptide is substantially similar to a second polypeptide if it shows sequence identity of at least about 75%–90% or greater when optimally aligned and compared using BLAST™ software (blastp) using default settings.

Figure 5:
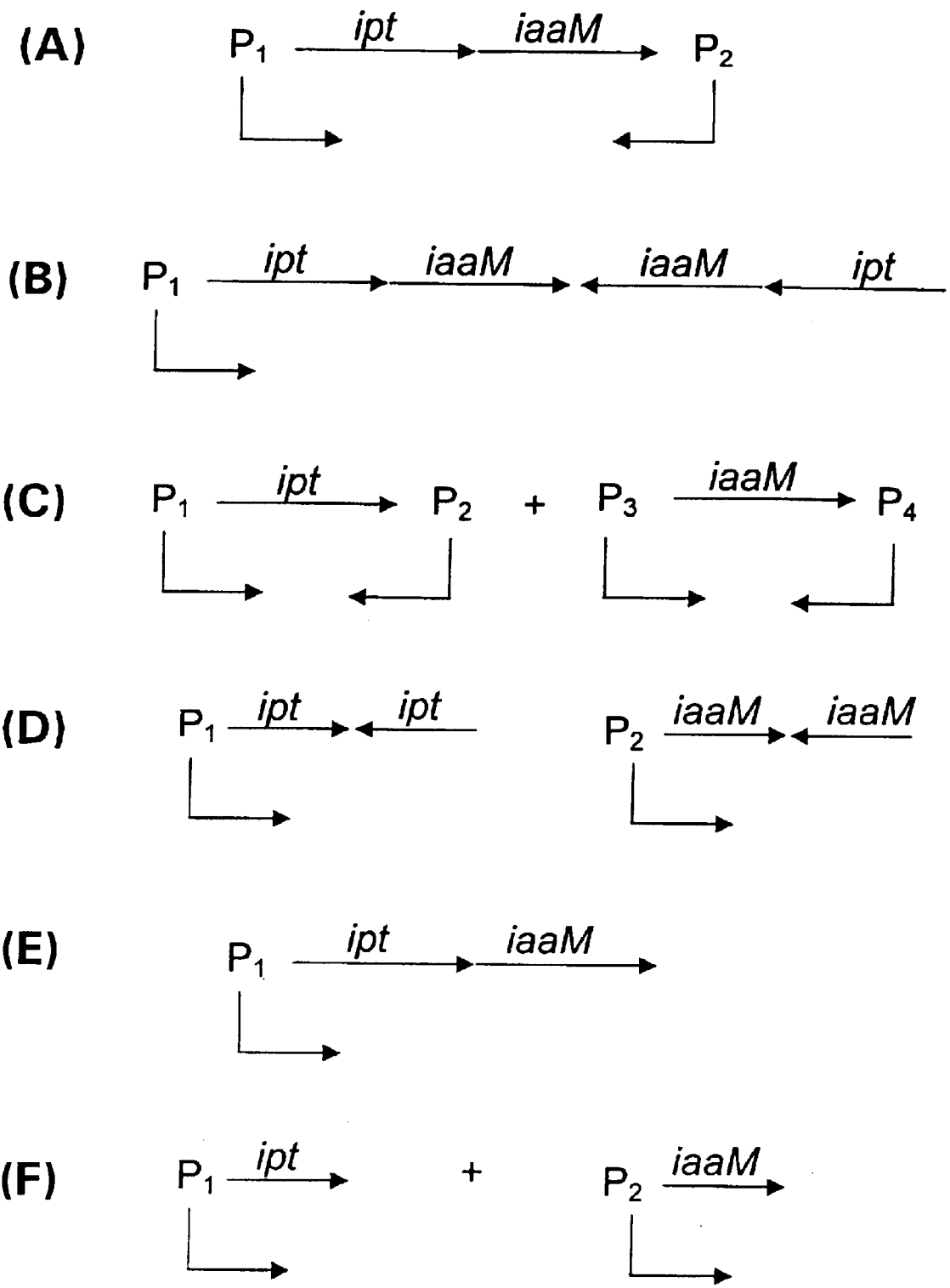
FIGS. 5(A)–5(F) depict several representative illustrations of bacterial-resistance constructs (BR construct) according to the invention. Promoters are designated by the capital letter "P" and the direction of expression is denoted by respective arrows. DNA sequences encoding untranslatable RNA molecules that target specific genes are indicated; however, one of ordinary skill in the relevant art will appreciate that untranslatable RNA molecules targeting other genes can be substituted.

Bacterial resistance construct (BR construct): A "bacterial resistance construct" (abbreviated "BR construct") is a sequence of DNA that incorporates at least one promoter and at least one DNA sequence encoding an untranslatable RNA (either double-stranded RNA, single-stranded RNA or a combination thereof). The arrangement of the promoter(s) in relationship to the DNA sequence(s) can vary. Representative configurations are illustrated in FIGS. 5(A)–5(G). FIG. 5(A) shows a BR construct in which one promoter (designated $P_1$) is used to express (direction of expression is indicated by the arrows) a DNA sequence encoding the sense-strand of a sequence that targets the ipt gene and the sense-strand of a sequence targeting the iaaM gene. This same construct also contains a second promoter (designated $P_2$) that drives the expression of the antisense-strand of the iaaM gene and the antisense-strand of the ipt gene. Thus, the combination of both promoters will generate a double-stranded RNA that contains a section targeting the ipt gene and a section targeting the iaaM gene. FIG. 5(B) shows a construct that contains one promoter ($P_1$) that expresses a DNA sequence that encodes several different untranslatable RNA sequences targeting both the ipt gene and the iaaM gene. Starting at the 5' end of the construct, the promoter $P_1$ drives the expression of a sense-strand targeting the ipt gene, a sense-strand targeting the iaaM gene, an antisense-strand targeting the iaaM gene, and a sense-strand targeting the ipt gene. This sequence can fold back on itself, and thus generate a double-stranded RNA molecule comprising regions homologous to both the ipt and iaaM gene. FIG. 5(C) shows another variation of a BR construct. This construct comprises independent promoters, $P_1$ and $P_2$, to drive the expression of an untranslatable RNA molecule in both the sense and anti-sense orientations, respectively. Two additional promoters ($P_3$ and $P_4$) are utilized for the expression of the sense and anti-sense strands of a second untranslatable RNA. FIG. 5(D) shows another variation of the BR construct. This construct comprises one promoter ($P_1$) to express first the sense-strand and then the antisense-strand of an untranslatable RNA molecule targeting the ipt gene. This construct also comprises a second promoter to express both the sense-strand and antisense-strand of an untranslatable RNA targeting the iaaM gene. FIGS. 5(E) and 5(F) illustrate additional variations that can be used to express single-stranded untranslatable RNA molecules. FIGS. 5(A)–(F) are intended to illustrate a few of various different promoter/DNA sequence combinations that are possible. A person of ordinary skill in the art will appreciate that many additional combinations can be used in BR constructs according to the invention.

II. General Description

The present method provides new and effective methods for suppressing the expression of Agrobacterium oncogenes. In particular, this invention is directed at, inter alia, producing plants that are capable of substantially inhibiting the formation of bacterially induced galls. These plants are produced by selecting a target gene of Agrobacterium origin, designing a nucleic acid (typically DNA) BR construct encoding untranslatable single-stranded RNA, double-stranded RNA, and/or untranslatable double-stranded RNA molecules having a high sequence identity to the target gene, and introducing at least one of these BR constructs into a host cell.

a. Selection of the Target Gene

There are many species of Agrobacterium, for example *Agrobacterium tumefaciens, Agrobacterium vitis, Agrobacterium rubi,* and *Agrobacterium rhizogenes.* The nucleic acid sequences of the respective oncogenes contained within these species are highly conserved. Therefore, a BR construct designed to encode at least one RNA molecule having high sequence identity to one or more target tumor-inducing Agrobacterium genes will likely confer resistance to at least one (typically multiple) species of Agrobacterium.

b. Producing a Nucleic Acid Construct Encoding an Untranslatable RNA

Practicing the present invention requires the manipulation of a DNA sequence using molecular biological techniques to produce the desired nucleic acid construct. The DNA sequence can be manipulated using standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR. Details of these techniques are provided in standard laboratory manuals such as Sambrook et al., *Molecular Cloning: A Laboratory Manual,* $2^{nd}$ ed., Cold Spring Harbor Laboratories, Cold Spring Harbor, N.Y., 1989, and Ausubel et al., *Short Protocols in Molecular Biology,* $2^{nd}$ ed., John Wiley and Sons, 1992.

Suppression of an oncogene using a method according to this invention is achieved by expressing, in a host cell, molecules of a BR construct having high sequence identity to the target gene(s). At least one molecule of the BR construct having substantial sequence identity to the target gene(s) is introduced into a host cell. The BR construct can be delivered into the host cell genome by delivering into the host a vector cell containing the BR construct.

Application of the present invention to construction of a BR construct desirably involves the selection of appropriate control sequences such as promoters, enhancers, and 3'-untranslated regions. The choice of which type of control sequence(s) to use in a BR construct will depend upon the particular tissue in which the BR construct will be expressed and the particular sequence(s) of the target gene(s). The variety of plant that is selected for transformation will also affect the choice of the control sequence(s), the vector, and the transformation method.

Constructing a suitable BR construct involves the selection of a DNA sequence that will be used to target at least one specific bacterial gene. Generally, the DNA sequence will encode an untranslatable RNA having at least 70% sequence identity with the target bacterial gene(s) (i.e., the gene(s) that will be suppressed).

In producing the BR construct, a DNA molecule homologous to a target a bacterial gene can be manipulated to render a single-stranded RNA or double-stranded RNA molecule encoded by the DNA molecule untranslatable. This can be done by, e.g., introducing any of various stop signals into the open reading frame of the DNA molecule to produce the BR construct. For example, the BR construct can be configured to contain one or more premature stop codons. A "stop codon" is a codon of the genetic code that signals ribosomes to terminate translation of a messenger RNA molecule. There are three stop codons in the genetic code: TAA, TAG, and TGA, as illustrated in Table 1 below.

TABLE 1

The Genetic Code

| First Position (5' end) | Second position | | | | Third Position (3' end) |
| --- | --- | --- | --- | --- | --- |
| | T | C | A | G | |
| T | Phe | Ser | Tyr | Cys | T |
| | Phe | Ser | Tyr | Cys | C |
| | Leu | Ser | STOP (och) | STOP | A |
| | Leu | Ser | STOP (amb) | Trp | G |
| C | Leu | Pro | His | Arg | T |
| | Leu | Pro | His | Arg | C |
| | Leu | Pro | Gln | Arg | A |
| | Leu | Pro | Gln | Arg | G |
| A | Ile | Thr | Asn | Ser | T |
| | Ile | Thr | Asn | Ser | C |
| | Ile | Thr | Lys | Arg | A |
| | Met | Thr | Lys | Arg | G |
| G | Val | Ala | Asp | Gly | T |
| | Val | Ala | Asp | Gly | C |
| | Val | Ala | Glu | Gly | A |
| | Val (Met) | Ala | Glu | Gly | G |

In the context of the foregoing discussion, a "premature" stop codon is located at a position transcriptionally upstream of a naturally occurring stop codon. Generally, the premature stop codon is positioned within 100 nucleotides of the translation-start codon, and typically within 50 nucleotides of the translation-start codon.

One or more stop codons can be inserted into the DNA sequence to produce the BR construct. Alternatively, the DNA sequence can be mutated to convert an existing triplet codon (encoding an amino acid) of the sequence into a stop codon. For example, the hypothetical DNA sequence:

CTT AAC TGG TCC would normally produce a corresponding RNA translated by ribosomes to produce the polypeptide:

Leu Asn Trp Ser The corresponding RNA can be rendered untranslatable by introducing a stop codon, such as TAA, into the DNA sequence. For example, the modified DNA sequence:

CTT TAA AAC TGG TCC encodes:

Leu STOP Alternatively, in the foregoing hypothetical DNA sequence, substitution of the ninth nucleotide (guanosine (G)) by adenosine (A) will result in the creation of a premature stop codon, rendering the corresponding RNA untranslatable, i.e., the following DNA sequence is produced:

CTT AAC TGA TCC which encodes:

Leu Asn STOP

Alternatively, the addition or deletion of one or more bases into or from, respectively, the DNA sequence (except multiples of three bases) can be used to displace the reading frame of the DNA sequence which can render the corresponding RNA molecule untranslatable. For example, the introduction of a single nucleotide (G) into the first codon of the foregoing hypothetical DNA sequence creates a new reading frame containing a premature stop codon:

CTG TAA CTG GTC C which encodes:

Leu STOP

An alternative manner of rendering an RNA molecule untranslatable is to remove the translation-initiation codon (usually ATG) from the corresponding DNA sequence. However, this method may result in use by ribosomes of an ATG codon elsewhere in the DNA sequence to initiate translation. Removal of the initiation codon ATG is, therefore, desirably used in conjunction with inserting one or more premature stop codons into a DNA sequence.

Another method of introducing a premature stop codon is by truncating the subject DNA sequence. This can be done, for example, by using a restriction enzyme to excise a portion of a target gene and then cloning only the excised portion of the gene into a vector. Transcription of the vector will produce a segment of homologous RNA effective to produce a co-suppression phenomenon, but will not produce a fully processed protein. Currently, the mechanism by which co-suppression works is not known. However, the phenomenon has been previously described in detail (Lindbo and Dougherty, *Virology* 189:725–733, 1992).

One or more of the above approaches may be used to render an RNA molecule encoded by a BR construct untranslatable. It will be appreciated that a very large number of sequence changes can be made in a suitable manner, the precise nature of which may depend on the actual DNA sequence being manipulated, to render the sequence of the corresponding RNA untranslatable. In certain embodiments, more than one stop codon may be introduced into the DNA sequence. For example, the resulting BR construct may contain a DNA sequence encoding untranslatable RNA that has been altered to contain at least one stop codon situated early in the open reading frame; the open reading frame is thus "truncated."

Many standard DNA mutagenesis techniques are available to modify DNA sequences in a manner as described above to produce the BR construct. The mutagensis techniques include, for example, M13 primer mutagenesis. Details of such techniques are provided in Sambrook et al., Chapter 15, *Molecular Cloning: A Laboratory Manual*, 2$^{nd}$ ed., Cold Spring Harbor Laboratories, Cold Spring Harbor, N.Y., 1989; and in Ausubel et al., Chapter 8, *Short Protocols in Molecular Biology*, 2$^{nd}$ ed., John Wiley and Sons, 1992.

According to another aspect of the invention, double-stranded RNA molecules are provided that are homologous to a target bacterial gene. Each strand of the double-stranded RNA can be produced from separate BR constructs, wherein a first BR construct encodes the antisense-strand and a second BR construct encodes the sense-strand. Upon transcription of the first and second BR constructs, the resulting sense-strand and corresponding antisense-strand form double-stranded RNA.

Alternatively, the sense-strand and antisense-strand can be produced from a single BR construct. The single BR construct can utilize two distinct promoters to initiate the expression of the antisense-strand and the sense-strand, or one promoter to drive expression of both strands. When a single promoter is utilized, both the sense-strand and the antisense-strand are normally produced as a single transcript, wherein the RNA sequence will fold back on itself to create a double-stranded RNA. Similarly, multiple combinations of promoters, antisense-strands, and sense-strands can be encoded on the same BR construct.

Double-stranded RNA can also be produced by transforming cells with a BR construct that encodes the sense-strand, a self-cleaving ribozyme, and the antisense-strand all on a single transcript. Upon transcription of such a BR construct, the sense-strand, the self-cleaving ribozyme, and the antisense-strand are produced. The self-cleaving ribozyme sequence folds back on the resulting transcript and splices the transcript between the sense- and antisense-strands, generating two independent complementary strands of RNA.

A proposed mechanism for suppressing a target bacterial gene by introducing into a host cell molecules of a BR construct having one or more sequences homologous to at least a portion of the target gene typically involves the activity of an inducible, cellular activity that degrades specific RNA sequences. This mechanism requires that the untranslatable single-stranded RNA, double-stranded RNA, and/or untranslatable double-stranded RNA encoded by the BR construct be recognizable by the RNA-specific cellular activity. To such end, the target DNA sequence and the DNA sequence of the BR construct desirably share a sequence identity.

In the Examples presented below, the DNA sequences of the respective BR constructs are derived directly from corresponding target bacterial nucleotide sequences. The sequences of the respective BR constructs differ from the corresponding target sequences primarily only by the presence (in the sequences of the BR constructs) of premature stop codons inserted by mutagenesis involving one or more frame-shift mutations. Thus, in these examples, the BR constructs have over 90% sequence identity to the corresponding target DNA sequences. However, a BR construct needs only to have sufficient sequence identity to the target gene so that the BR construct confers disease resistance to the host cell. Therefore, a BR construct that encodes an RNA molecule having less than 90% sequence identity to the corresponding target DNA sequence can be used. In any event, the BR construct typically has at least 60% sequence identity to the corresponding target DNA molecule, and in some cases at least 70%, 75%, or 80% sequence identity to the target DNA molecule.

The following examples also describe BR constructs in which the DNA sequence corresponds to 700 base pairs of the ORF (open reading frame) of the target gene. It will be understood, however, that the untranslatable RNA provided by the BR construct need not correspond specifically to 700 base pairs of the ORF of the target gene; substantially shorter sequences of untranslatable RNA may also be effective.

The BR construct should be sufficiently long and share a sufficient level of sequence identity to the target gene such that the BR construct confers disease resistance to the host cell. The ability of a particular BR construct to confer disease resistance to a host cell can readily be determined by using the assay described below, in which a transgenic plant is challenged with a bacterial pathogen. Typically, the ORF of the DNA sequence of the BR construct is at least 25–100 nucleotides in length, although longer sequences, such as 100–250, 250–500, or greater than 500 nucleotides may be used and may provide superior results. In embodiments where shorter sequences (i.e., less than 250 nucleotides) are utilized, the respective BR constructs will likely share a high degree of sequence identity (e.g., at least 60% sequence identity) with the target gene sequence.

The present invention can be used to suppress the expression of a bacterial tumor gene in a plant cell. To such end, the plant cell is transformed with a BR construct having a high sequence identity to a target bacterial gene. The molecule of the BR construct encodes one or more untranslatable single-stranded RNA and/or double-stranded RNA molecules. The BR construct can comprise a sequence of at least 25 nucleotides in length having at least 60% sequence identity to the target bacterial gene. Alternatively, the BR construct can comprise a sequence of at least 100 nucleotides in length having at least 60% sequence identity to the target bacterial gene. Furthermore, the BR construct can comprise a nucleic acid sequence of at least 250 nucleotides in length having at least 60% sequence identity to the target bacterial gene.

The present invention is not limited to the suppression of a single target bacterial gene. Rather, it is possible to suppress, according to the invention, the expression of multiple target genes using one or more BR constructs that comprise DNA sequences corresponding to several respective genes expressed in the target cell. This approach can be used to enhance resistance to a single bacterial strain or to produce resistance to multiple strains of bacteria in a single plant. As illustrated in the Examples below, the formation of a gall on a plant by a pathogenic bacterium infecting the plant can be reduced or eliminated by the introduction into the cells of the plant, a BR construct having a high sequence identity to at least one gene of the infecting bacterium. This approach allows the production of transgenic plants resistant to the bacterium.

c. Vectors

It will be appreciated that the efficacy of the present invention depends on transcription of the DNA sequence of the BR construct introduced into a host plant cell. Transcription of a DNA sequence into messenger RNA is preferably effected by including a promoter region at the 5' end of the DNA sequence of the BR construct, together with regulatory sequences at the 3' end of the DNA sequence. Many promoter sequences and 3'-regulatory sequences have been identified and characterized in a wide range of viral, bacterial, fungal, plant, and animal genes. Therefore, the selection of suitable promoter and a suitable 3'-regulatory sequence is within the capability of a person of ordinary skill in the relevant art.

After choosing and incorporating the appropriate regulatory DNA sequence(s) into the BR construct, the BR construct is incorporated into a suitable vector for introduction into the host cell. The choice of regulatory sequences, as well as the choice of a suitable transformation vector will depend upon the type of host cell into which the BR construct is to be introduced and upon the desired transformation method for the host cell. Vectors suitable for transforming plant cells (derived from either monocotyledonous or dicotyledonous plants) are described below. Transformation of both monocotyledonous and dicotyledonous plant cells is now routine and the selection of the most appropriate transformation technique will be determined by the skilled practitioner.

A number of promoters that are active in plant cells have been described in the literature. Promoters that are known to cause transcription of DNA in plant cells can be used to suppress gene expression in plants. Such promoters can be obtained from plant cells or from plant viruses and include, but are not limited to, the CaMV (cauliflower mosaic virus) 35S promoter. It is desirable that the chosen promoter be capable of causing sufficient expression of the BR construct to produce sufficient RNA to suppress expression of the target gene. The amount of RNA needed to suppress expression of a particular target gene may vary from one target gene to another, expression level of the particular target gene, and the plant type. Accordingly, whereas the CaMV promoter is employed in the Examples presented below, it will be understood that this promoter may not be optimal for all embodiments of the present invention.

The vector can be configured to optimally exploit the promoter and termination sequences in the target gene itself. Used in this way, the target-gene promoter is not altered and the subsequent stop signals are introduced into the ORF of the target gene. Additionally, the termination signals of the target gene can be left intact. This configuration permits increasing the transcription of untranslatable RNA and/or double-stranded RNA whenever the factors necessary for transcription of the target gene are present.

The promoter(s) used in a BR construct according to the invention may be modified, if desired, to include additional regulatory sequence(s). Such additional regulatory sequences can confer, e.g., specificity to the respective promoter region. For example, the small subunit of the ribulose bis-phosphate carboxylase ("ss RUBISCO") gene is expressed in plant leaves but not in root tissues. A sequence motif that represses the expression of the ss RUBISCO gene in the absence of light (to create a promoter which is active in leaves but not in root tissue), has been identified. This and/or other regulatory sequences such as the HSP70 leader sequence from petunia, may be ligated to promoters such as the CaMV 35S, or figwort mosaic virus (FMV) promoter, to modify the expression patterns of a gene.

The 3'-nontranslated region (that functions as a polyadenylation site for RNA in plant cells) of a gene can also be used in the present invention. Such 3'-non-translated regions include, but are not limited to, the 3'-transcribed (but non-translated) region of the CaMV 35S gene, the pea-rbcS E9 3'-non-translated region, the NOS 3'-non-translated region, and one or more of the 3'-transcribed, non-translated (but non-translated) regions containing the polyadenylation signals of the tumor-inducing (Ti) genes of Agrobacterium, such as the tumor morphology large (tml) gene.

d. Plant Species

Gall formation in plants can be induced by any of various organisms. For example, galls can be induced by bacteria from the genus Agrobacterium, and certain species of Pseudomonas, Rhizobacter, and Rhodococcus.

In the case of Agrobacterium, gall formation is caused by genes introduced into the plant cells on the Ti plasmid provided by an infecting bacterium. There are a variety of naturally occurring Ti plasmids that can give rise to different types of galls. Galls are normally caused by *A. tumefaciens* which infects over 391 genera of plants including shrubs, fruit trees, nut trees, tuber-producing plants, conifers, grape vines, chrysanthemums, roses, cane berries, nursery crops, and commercially important plants (Bradbury, J. F. Guide to Pathogenic Bacteria. CAB International, Slough, Britain, 1986). Hairy root is another type of gall induced by *A. rhizogenes*, that primarily affects the roots of apple trees. Finally, *Agrobacterium rubi* can infect both raspberries and black berries, and give rise to cane galls. (Agrios, *Plant Pathology*, Academic Press, 1997).

e. Transformation

A BR construct according to the present invention is introduced into a plant cell using a suitable vector and transformation method as described below. The resulting transformed cells can then be allowed to regenerate into whole plants. Any of various conventional methods employed for transforming plant cells to generate transgenic plants, including stably transformed plants, can be used in this invention. The choice of method will typically vary with the type of plant to be transformed; persons skilled in the art will recognize the suitability of particular methods for given plant types. Suitable methods may include, but are not limited to: electroporation of plant protoplasts; liposome mediated transformation; polyethylene glycol-mediated transformation; transformation using viruses; microinjection of plant cells; microprojectile bombardment of plant cells and *Agrobacterium tumefaciens* (AT)-mediated transformation. The DNA sequences comprising the CaMV 35S promoter and CAMV 35S non-translated 3' region and the mutated cDNA encoding a untranslatable RNA can be combined in a single cloning vector. This vector can be transformed subsequently into, e.g., cultured tobacco cells.

f. Conferred Resistance

The mechanism of co-suppression is unknown. However, transgenic tissue containing a co-suppression gene can be grafted onto a non-transgenic plant The graft then confers resistance to the non-transgenic plant (Jorgensen et al., *Science*, 279:1486–87, 1998). Furthermore, this "conferred resistance" can be established by either grafting a scion (upper vegetative tissue) onto a transgenic stock (lower vegetative tissue), or by grafting a transgenic scion onto a non-transgenic stock. This conferred resistance can be transmitted through at least 30 cm of non-transgenic tissue.

It is possible that the phenomenon of conferred resistance may allow resistance to gall formation to be introduced into existing plants. Thus, a mature plant can be made resistant to gall formation by grafting transgenic tissue onto the plant. Furthermore, several grafts can be placed independently on the plant to produce resistance in the plant to several different bacterial pathogens.

A grafting protocol can be made more flexible by utilizing cross-species grafting. Thus, a graft from, e.g., almond (*Prunus amygdalus*) can be placed on stock from peach (*Prunus persica*). Such flexibility increases the range of plants for which a given transgenic tissue can be used. For example, after almond tissue containing the desired BR construct has been generated, the tissue can be used to confer resistance not only to other almond trees, but also to peach trees.

The use of conferred resistance also decreases the possibility that a transgene made according to the invention will be introduced into the environment. This is because the resistance is derived from the graft itself and the rest of the plant remains free of the transgene. Therefore, the fruits and seeds of the plant can be left non-transgenic, so as not to transmit the gene.

By preventing a transgene from being systemically introduced into the plant, products for human consumption can be produced by the plant that are not transgenic.

Figure 3:
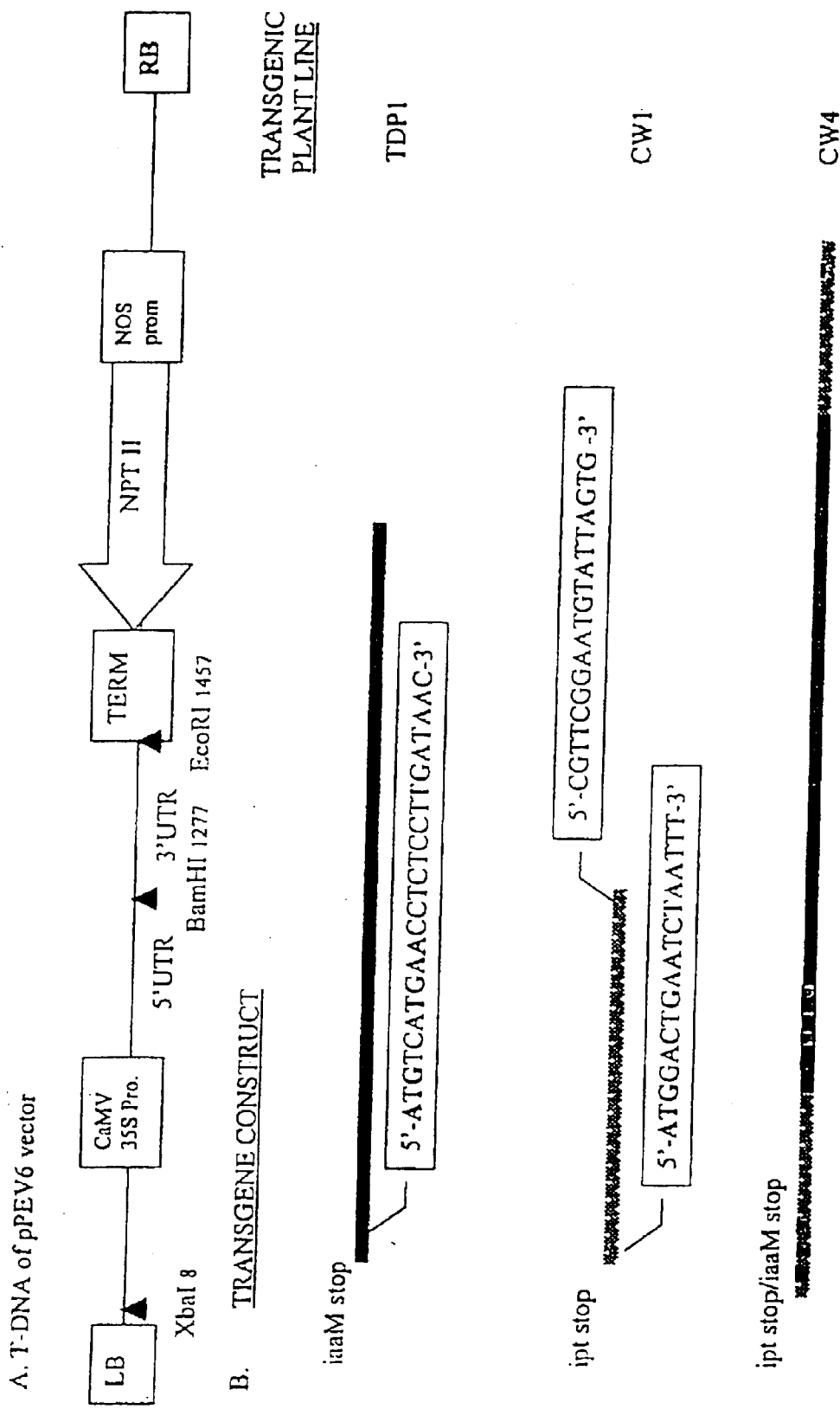
FIG. 3 is a diagram of the binary plant transformation vector (pPEV6) (panel A) and of mutant transgenes that can be used to elicit co-suppression of T-DNA oncogenes. "RB" and "LB" denote right and left T-DNA border sequences, respectively. NOS prom/NPTII denotes the nopaline synthase promoter fused to the neomycin phosphotransferase II gene (conferring kanamycin resistance). 5' UTR and 3' UTR denote the 5' and 3' untranslated regions, respectively, associated with the cauliflower mosaic virus promoter (CAMV 35S Pro). Arrowheads denote respective restriction sites for XbaI, BamHI, and EcoRI; numbers indicate respective coordinates relative to the vector sequence. Premature stop codons are shown in bold, whereas natural start codons are shown in plain text.

III. EXAMPLES a. Construction of BR Constructs Encoding Untranslatable RNA molecules To produce a DNA construct capable of eliciting co-suppression, the iaaM and ipt oncogenes were modified by changing the third codon of each gene to a stop codon and introducing a frameshift mutation downstream of each respective introduced stop codon, thereby creating additional stop codons in the reading frame (FIG. 3). The polymerase chain reaction (PCR) primer oligonucleotides used to create these mutations in the DNA construct are described in Table 2. The primers used to modify the ipt gene resulted in the deletion of the 5' C of the third codon and changed the 3' G of the third codon to an A. The iaaM modifications introduced the stop sequence TGA at the third codon and the two bases following the third codon were deleted. A second DNA construct was made that contained a hybrid transgene configured to elicit co-suppression of both ipt and iaaM. The second DNA construct was made by digesting a vector (containing the ipt-stop mutation) and a vector containing the iaaM-stop mutation with BamH1. The fragment containing the iaaM-stop mutation was then ligated into the fragment containing the ipt-stop mutation, thereby yielding a BR construct containing the mutant iaaM gene inserted into the mutant ipt gene (FIG. 3). The sequence of each DNA construct was verified, and the BR construct was inserted into a plant-transformation vector (pPEV6; Lindbo and Dougherty, *Mol. Plant-Microbe Interact.* 5:144–153, 1992) oriented such that the sense-strand of each mutant was expressed from the cauliflower mosaic virus (CaMV 35S) promoter (FIG. 3).

TABLE 2

PCR Primers Used to Produce Mutant iaaM and ipt Genes

Figure 4:
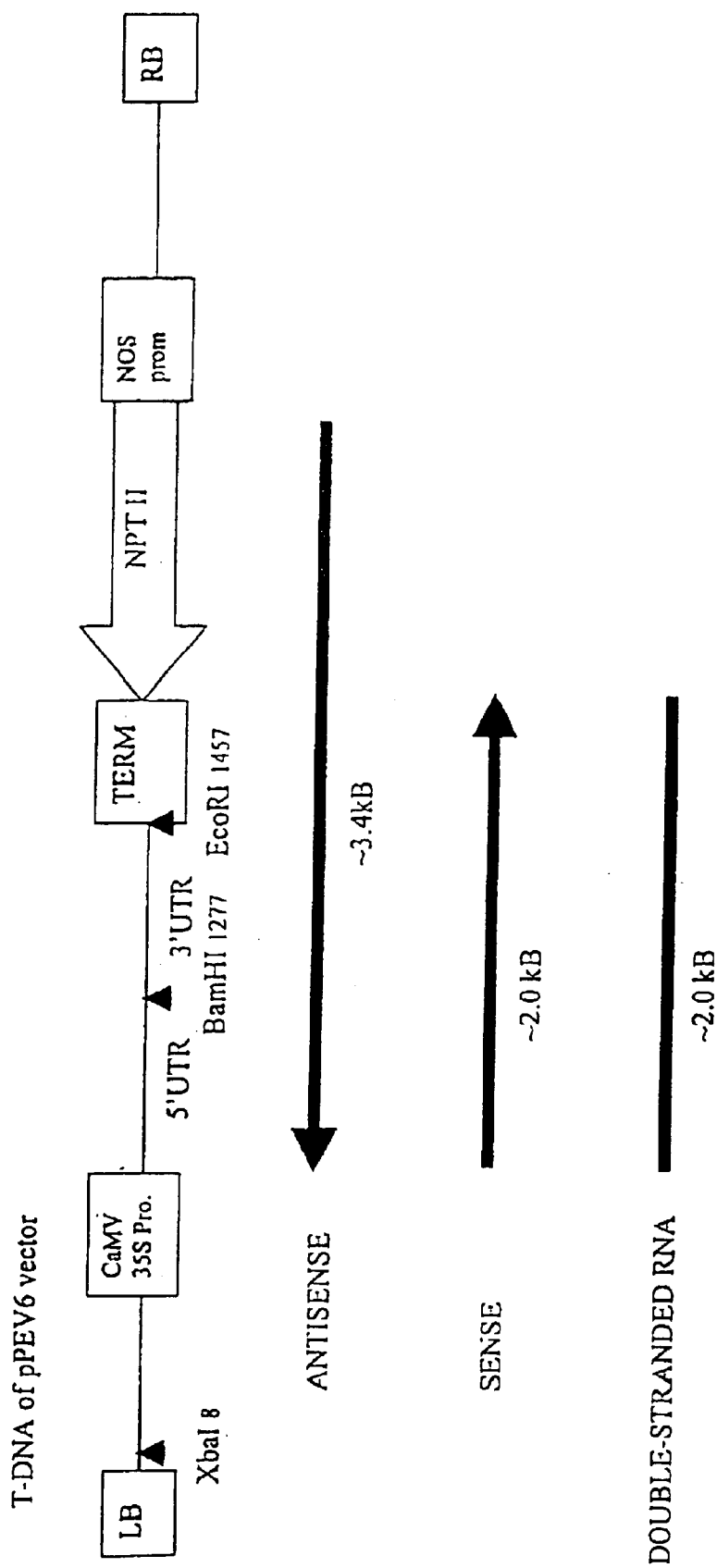
FIG. 4 illustrates the most likely scenario for the creation of double-stranded RNA. The sense strand is transcribed from the CaMV 35S promoter and the anti-sense strand is transcribed from the NOS promoter.

| Primers | | Sequence |
|---|---|---|
| iaaM stop | 5' primer | 5'-CGGGATCCATGTCATGAACCTCTCCTTGA TAAC-3' (SEQ ID NO: 1) |
| | 3' primer | 5'-CGGGATCCTGCGACTCATAGT-3' (SEQ ID NO: 2) |
| ipt stop | 5' primer | 5'-GAAGATCTGATCATGGACTGAATCTAAT TTTCGGTCC-3' (SEQ ID NO: 3) |
| | 3' primer | 5'-GAAGATCTGATCACTAATACATTCCGAAC GG-3' (SEQ ID NO: 4) | b. Construction of Double-Stranded RNA and Untranslatable Double-Stranded RNA Vectors A vector encoding an iaaM-stop mutation (i.e., a DNA construct modified to incorporate a stop codon at the third codon, followed by a two base pair deletion) exhibited evidence of bacterial resistance. This resistance was derived from the production of double-stranded RNA by transcription of the vector (FIG. 4). The sense-strand of the double-stranded RNA was transcribed from the CaMV 35S promoter and the antisense-strand was probably transcribed from the nopaline synthase promoter (NOS). Thus, this vector can produce a long double-stranded RNA that is approximately 2,000 bp long. Evidence of such a double-stranded RNA was found in northern blots that showed partially degraded antisense-strands ranging in size from 3.4 Kb to less than 0.24 Kb. As is depicted in FIG. 4, the double-stranded RNA appeared to include an approximately 2,000 bp long region that was 100% homologous to the iaaM sequence. Therefore, bacterial resistance observed in iaaM-transgenic plants is probably attributable to the presence of the double-stranded RNA. This resistance does not appear to have been due solely to the presence of the introduced stop codon.

Double-stranded RNA is capable of suppressing endogenous plant genes, as well as suppressing viral infection (Ruiz et al., *Plant Cell* 10:937–946, 1998). However, the suppression, via double-stranded RNA and/or untranslatable RNA, of disease symptoms caused by bacteria, such as Agrobacterium, has previously not been shown.

C. Production of Plants Homozygous for Untranslatable RNA Transgenes

Mutant iaaM (SEQ ID NO: 7), ipt (SEQ ID NO: 5), and ipt/iaaM genes (SEQ ID NO: 9) were introduced separately into haploid tobacco (*N. tabacum*, "Burley" and "Kentucky" cultivars). The chromosomes of kanamycin-resistant transformants of these plants were doubled to produce plants homozygous for each transgene. These plants were the subjects of initial tests, which were repeated on the F1 progeny of self pollinations.

d. Gall-resistant Plant Phenotypes

Putative iaaM-suppressing plants (designated "TDP1" lines) were challenged with ipt-mutant *A. tumefaciens* (strain 338; Garfinkel et al., Cell 27:143–153, 1981). Of 63 lines tested, 35 lines, including TDP1-B7 & TDP1-B17, suppressed the wild-type iaaM gene on *A. tumefaciens* T-DNA introduced into such plants, thereby preventing tumorous growth in the respective plants. When inoculated with wild-type *A. tumefaciens* (strain A348; Garfinkel et al., Cell 27:143–153, 1981), each of the 35 lines produced "shooty" galls typical of cytokinin-driven tumors, such as those induced on wild-type plants inoculated with iaaM-mutant *A. tumefaciens* (Ream et al., *Proc. Natl Acad Sci. USA* 80:1660–1664, 1983; and Garfinkel et al., Cell 27:143–153, 1981). Thus, the plants that produced shooty galls exhibited the phenotype expected of a transgenic plant capable of suppressing iaaM.

Putative ipt-suppressing plants (designated "CW1" lines) were challenged with iaaM-mutant *A. tumefaciens* (strain 328; Garfinkel et al., Cell 27:143–153, 1981). Of 45 lines investigated, one (designated "CW1-K27") clearly suppressed the wild-type ipt gene on introduced *A. tumefaciens* T-DNA. Another 6 lines exhibited similar results in initial tests on the original transgenic plants, but these lines were lost before seeds were obtained. The ipt-suppressing plant (CW1-K27), when inoculated with wild-type *A. tumefaciens*, produced small necrotic galls typical of auxin-driven tumors, such as those induced on wild-type plants inoculated with ipt-mutant *A. tumefaciens* (Ream et al., *Proc. Natl. Acad. Sci. USA* 80:1660–1664, 1983; Garfinkel et al., Cell 27:143–153, 1981). There were 30 lines tested (designated "CW4" lines) that contained the hybrid ipt-iaaM transgene. One line (designated "CW4-B30") exhibited a significant reduction in tumorigenesis when inoculated with either wild-type, iaaM-mutant, or ipt-mutant *A. tumefaciens*. Although the CW4-B30 line exhibited markedly reduced gall size and absence of gall formation at some inoculation sites, gall tumorigenesis was not entirely absent. The controls were kanamycin-resistant plant lines (designated "PEV6" lines) that contained the transformation vector T-DNA (from pPEV6) without a transgene located downstream of the CaMV 35S promoter. As expected, none of these lines exhibited any suppression of T-DNA oncogenes upon infection with *A. tumefaciens*.

e. Molecular Analysis of Transgenic Plants

To examine transgene copy number and structural integrity, Southern blot analyses were performed on representative plant lines of each type. Most lines contained several copies of the transgene, and all lines contained one or more intact copies (see Tables 3, 4, and 5, below). Some lines also contained rearranged copies of the transgene, which were identified by the presence of multiple bands in the Southern blots.

TABLE 3

Southern Blot of Genomic DNA Digested with BamH1

| Transgenic Plant | 1799-bp Transgene Fragment (+/−)* | Oncogene Suppression (+/−)* |
|---|---|---|
| CW4 B1 (ipt-stop/iaaM-stop) | + | − |
| CW4 B11 (ipt-stop/iaaM-stop) | + | − |
| CW4 B22 (ipt-stop/iaaM-stop) | + | − |
| CW4 B30 (ipt-stop/iaaM-stop) | + | +/− |
| TDP1 B7 (iaaM-stop) | + | + |
| TDP1 B17 (iaaM-stop) | + | + |
| TDP1 B27 (iaaM-stop) | + | + |
| TDP1 B31 (iaaM-stop) | + | − |
| PEV6 B2 (vector alone) | − | − |
| PEV6 B14 (vector alone) | − | − |

*+ denotes the presence of the transgene fragment or the suppression of oncogene expression.
− denotes the absence of the transgene fragment or the absence of oncogene expression.

TABLE 4

Southern Blot of Genomic DNA Digested with EcoR1

| Transgenic Plant | Transgene Copy Number | Oncogene Suppression (+/−)* |
|---|---|---|
| TDP1 B7 (iaaM-stop) | 3–4 | + |
| CW4 B1 (ipt-stop/iaaM-stop) | 2 | − |
| CW4 B11 (ipt-stop/iaaM-stop) | 2 | − |
| CW4 B22 (ipt-stop/iaaM-stop) | 2 | − |
| CW4 B30 (ipt-stop/iaaM-stop) | 4 | +/− |
| TDP1 B17 (iaaM-stop) | 2 | + |
| TDP1 B27 (iaaM-stop) | 1 | + |
| TDP1 B31 (iaaM-stop) | 4< | + |
| PEV6 B2 (vector alone) | 0 | − |
| PEV6 B14 (vector alone) | 0 | − |

*+ denotes the presence of the transgene fragment or the suppression of oncogene expression.
− denotes the absence of the transgene fragment or the absence of oncogene expression.

TABLE 5

Southern Blot of Genomic DNA Digested with either Hinf1 or EcoR1 Digested Genomic DNA

| Transgenic Plant | Presence of Restriction Fragment (+/−)* | Restriction Enzyme | Suppression of Oncogenes (+/−)* |
|---|---|---|---|
| CW1 K27 (ipt-stop) | + | Hinf1 | + |
| CW1 K27 (ipt-stop) | + | EcoR1 | + |
| CW1 K52 (ipt-stop) | + | Rinf1 | − |
| CW1 K52 (ipt-stop) | + | EcoR1 | − |

*+ denotes the presence of the transgene fragment or the suppression of oncogene expression.
− denotes the absence of the transgene fragment or the absence of oncogene expression.

The foregoing results show that co-suppression drastically reduces accumulation of mRNA encoded by the eliciting transgene and mRNA encoded by other genes that contain sufficient (approximately 70% or more) sequence similarity (Marano and Baulcombe, Plant J. 13:537–546, 1998). Hence, Northern blot analysis was used to measure mRNA accumulationi(but not transcription rate). In all iaaM-suppressing lines that were examined, transgene mRNA was undetectable, as expected, using a strand-specific hybridization probe. However, full-length and degraded antisense RNA molecules that included the transgene sequences were detected using a double-stranded hybridization probe. These transcripts appear to have initiated from the vector's nopaline synthase promoter and continued through both the neomycin phosphotransferase genc (in the sense direction) and the iaaM transgene (in the antisense direction). In the successful ipt-suppressing line, a trace amount of transgene-encoded mRNA was detected. Another line that contained the ipt transgene accumulated a large amount of transgene mRNA, but this line failed to co-suppress an incoming A. tumefaciens T-DNA-bome ipt gene. Plants that contained the hybrid ipt-iaaM transgene accumulated varying quantities of transgene-encoded mRNA. As expected, most of these lines did not elicit any co-suppression and only one line elicited partial co-suppression.

f. Discussion

By studying the ability of wild-type and iaaM- or ipt-mutant A. tumefaciens to induce tumors on various lines of transgenic plants, it has been shown that: 1) many lines suppressed an incoming T-DNA iaaM gene, 2) one line suppressed an incoming T-DNA ipt gene, and 3) one line partially suppressed both ipt and iaaM genes simultaneously.

By combining successful iaaH- or iaaM-suppressing transgenes with an ipt-suppressing transgene in a single plant line, a transgenic plant fully resistant to gall formation can be produced. This can be done through standard breeding techniques, in which a cross between lines homozygous for the individual genes is performed. The F2 generation will include plants homozygous for both transgenes; such plants are expected to substantially resistant to gall formation. This expectation is supported by data from a plant that contained the hybrid ipt-iaaM transgene. This plant nearly prevented gall formation, indicating that a single hybrid gene can elicit co-suppression against two target oncogenes.

The transgenes used in this study will likely elicit co-suppression against a broad variety of Agrobacterium species, as well as various strains of such species. This allows the production of plants (such as grape vines, fruit trees, nut trees, and chrysanthemums) that are resistant to gall formation. Other studies have established that approximately 70% sequence identity is required to elicit co-suppression (Marano and Baulcombe, Plant J. 13:537–546, 1998). Fortunately, the target T-DNA oncogenes (iaaM and ipt) are highly conserved among diverse A. tumefaciens strains. Even limited-host-range grape-specific A. vitis strains have greater than 90% sequence identity with the octopine-type oncogenes used in our study (Otten and DeRuffray, Mol. Gen. Genet. 245:493–505,1994).

Having illustrated and described the principles of the invention in multiple embodiments and examples, it should be apparent to those skilled in the art that the invention can be modified in arrangement and detail without departing from such principles. Therefore, the invention encompasses all modifications coming within the spirit and scope of the following claims.

What is claimed is:

1. A method of producing a plant cell that is resistant to gall disease, the method comprising transforming a plant cell with a nucleic acid molecule haviny the sequence as set forth in resides 1 through 1801 of SEQ ID NO: 10, but wherein the nucleic acid molecule comprises a stop sequence at the third codon and a deletion of the two bases following the third codon, and wherein the nucleic acid molecule encodes a double-stranded RNA molecule, thereby producing a plant cell that is resistant to gall disease.

2. A plant-transformation vector, comprising the nucleic acid molecule of claim 1.

3. A plant cell transformed with the plant-transformation vector of claim 2.

4. A differentiated plant, comprising plant cells produced according to the method of claim 1.

5. A method of producing a plant resistant to gall disease caused by Agrobacterium, comprising:

transforming at least one plant cell with a nucleic acid molecule having the sequence as set forth in residues 1 through 1801 of SEO ID NO: 10, but wherein the nucleic acid molecule comprises a stop sequence at the third codon and a deletion of the two bases following the third codon, and wherein the nucleic acid molecule encodes a double-stranded RNA molecule, growing at least one plant from at least one transformed plant cell; and selecting a plant that shows a reduced susceptibility to gall disease caused by Agrobacterium, thereby producing a plant resistant to gall disease caused by Agrobacterium.

6. A plant resistant to gall disease caused by Agrobacterium, produced by the method of claim 5.

7. A chimeric plant, comprising at least one non-transformed plant cell grafted to the plant of claim 6.

8. A plant resistant to gall disease produced by sexual or asexual reproduction of the plant of claim 6 wherein the plant comprises the nucleic acid molecule used to transform the plant cell.

9. A seed produced by selfing or outcrossing the plant of claim 6, wherein the seed comprises the nucleic acid molecule used to transform the plant cell.

10. A recombinant nucleic acid molecule comprising the nucleic acid sequence as set forth in residues 1 through 1801 of SEQ ID NO: 10, but wherein the nucleic acid sequence comprises a stop sequence at the third codon and a deletion of two bases following the third codon, and wherein the nucleic acid sequence encodes a double-stranded RNA molecule, wherein the recombinant nucleic acid molecule, when introduced into and transcribed in a plant, makes the plant resistant to gall disease.

11. A vector, comprising the recombinant nucleic acid molecule of claim 10.

12. A transgenic plant cell transformed with the vector of claim 11.

13. A transgenic plant, comprising at least one transgenic cell transformed with a recombinant nucleic acid molecule, as recited in claim 12.

14. The transgenic plant of claim 13, wherein the plant is selected from the group consisting of apricot, blackberry, pear, peach, plum, blueberry, cherry, kiwi, quince, raspberry, and rose.

15. A chimeric plant, comprising at least one transgenic plant cell as recited in claim 12.

16. The transgenic plant of claim 13, wherein the plant is chrysanthemum.

17. The transgenic plant of claim 13, wherein the plant is selected from the group consisting of conifers and poplars.

18. The transgenic plant of claim 13, wherein the plant is an ornamental shrub.

19. The transgenic plant of claim 13, wherein the plant is selected from the group consisting of almond, apple, grape, and walnut.

20. The recombinant nucleic acid molecule of claim 10, wherein the nucleic acid sequence is operably linked 5-prime to a 35S CaMV promoter and 3-prime to a NOS promoter.

21. A method of producing a plant cell that is resistant to gall disease, the method comprising transforming a plant cell with a nucleic acid molecule having the sequence as set forth in SEQ ID NO: 10, but wherein the nucleic acid molecule comprises a stop codon at the third codon and a deletion of the two bases following the third codon, and wherein the nucleic acid molecule encodes a double-stranded RNA molecule, thereby producing a plant cell that is resistant to gall disease.

22. A method of producing a plant resistant to gall disease caused by Agrobacterium, comprising:

transforming at least one plant cell with a nucleic acid molecule having the sequence as set forth in SEQ ED NO: 10, but wherein the nucleic acid molecule comprises a stop codon at the third codon and a deletion of the two bases following the third codon, and wherein the nucleic acid molecule encodes a double-stranded RNA molecule, growing at least one plant from at least one transformed plant cell; and selecting a plant that shows a reduced susceptibility to gall disease caused by Agrobacterium, thereby producing a plant resistant to gall disease caused by Agrobacterium.

23. A recombinant nucleic acid molecule comprising the nucleic acid sequence as set forth in SEQ ID NO: 10, but wherein the nucleic acid sequence comprises a stop codon at the third codon and a deletion of two bases following the third codon, and wherein the nucleic acid sequence encodes a double-stranded RNA molecule, wherein the recombinant nucleic acid molecule, when introduced into and transcribed in a plant, makes the plant resistant to gall disease.

* * * * *

UNITED STATES PATENT AND TRADEMARK OFFICE
CERTIFICATE OF CORRECTION

PATENT NO. : 6,759,574 B1
DATED : July 6, 2004
INVENTOR(S) : Ream et al.

It is certified that error appears in the above-identified patent and that said Letters Patent is hereby corrected as shown below:

Title page,
Item [56], References Cited, OTHER PUBLICATIONS, "Sitbon et al." reference, "*tumefaciens*iaaH" should be -- *tumefaciens* iaaH --.

Column 2,
Lines 40-41, "*MicrobioL* Sci" should be -- *Microbiol Sci* --.

Column 3,
Line 1, "iaah" should be -- iaaH --.

Column 4,
Lines 40-41, "(CAMV 35S Pro)" should be -- (CaMV 35S Pro) --.

Column 5,
Line 43, "CDNA" should be -- cDNA --.
Line 56, "fumctional" should be -- functional --.

Column 14,
Line 18, "CAMV" should be -- CaMV --.

Column 15,
Line 12, "BamH1" should be -- BamHI --.
Line 53, "sizc" should be -- size --.

Column 17,
Line 32, Table 4, "TDP1 B31 (iaaM-Stop)  4<   -" should be
            -- TDP1 B31 (iaaM-Stop)  4<   + --.

UNITED STATES PATENT AND TRADEMARK OFFICE
CERTIFICATE OF CORRECTION

PATENT NO. : 6,759,574 B1
DATED : July 6, 2004
INVENTOR(S) : Ream et al.

It is certified that error appears in the above-identified patent and that said Letters Patent is hereby corrected as shown below:

Column 29,
Line 49, "haviny" should be -- having --.
Line 50, "resides" should be -- residues --.

Signed and Sealed this

Twenty-first Day of March, 2006

JON W. DUDAS
*Director of the United States Patent and Trademark Office*

SEQUENCE LISTING

<160> NUMBER OF SEQ ID NOS: 12

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: PCR Primer

<400> SEQUENCE: 1
cgggatccat gtcatgaacc tctccttgat aac            33

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: PCR Primer

<400> SEQUENCE: 2
cgggatcctg cgactcata            19

<210> SEQ ID NO 3
<211> LENGTH: 37
<212> TYPE: DNA
<213> ORGANISM: Artificial Sequence
<220> FEATURE:
<223> OTHER INFORMATION: Description of Artificial Sequence: PCR Primer

<400> SEQUENCE: 3
gaagatctga tcatggactg aatctaattt tcggtcc            37

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: PCR Primer

<400> SEQUENCE: 4
gaagatctga tcactaatac attccgaacg g            31

<210> SEQ ID NO 5
<211> LENGTH: 747
<212> TYPE: DNA
<213> ORGANISM: Agrobacterium tumefaciens

<400> SEQUENCE: 5
gaagatctga tcatggactg aatctaattt tcggtccaac ttgcacagga agacgacga      60 ccgcgatagc tcttgcccag cagacagggc ttccagtcct ttcgcttgat cgggtccaat    120
gctgtcctca actatcaacc ggaagcggac gaccaacagt ggaagaactg aaaggaacga    180
cgcgtctcta ccttgatgat cggcctctgg tgagggtat catcgcagcc aagcaagctc     240
atcataggct gatcgaggag gtgtataatc atgaggccaa cggcgggctt attcttgagg    300
gaggatccac ctcgttgctc aactgcatgg cgcgaaacag ctattggagt gcagattttc    360
gttggcatat tattcgccac aagttacccg accaagagac cttcatgaaa gcggccaagg    420
ccagagttaa gcagatgttg caccccgctg caggccattc tattattcaa gagttggttt    480
atctttggaa tgaacctcgg ctgaggccca ttctgaaaga gatcgatgga tatcgatatg    540
ccatgttgtt tgctagccag aaccagatca cggcagatat gctattgcag cttgacgcaa    600

-continued

```
atatggaagg taagttgatt aatgggatcg ctcaggagta tttcatccat gcgcgccaac      660
aggaacagaa attcccccaa gttaacgcag ccgctttcga cggattcgaa ggtcatccgt      720
tcggaatgta ttagtgatca gatcttc                                          747
```

<210> SEQ ID NO 6
<211> LENGTH: 2
<212> TYPE: PRT
<213> ORGANISM: Agrobacterium tumefaciens

<400> SEQUENCE: 6

Met Asp
  1

<210> SEQ ID NO 7
<211> LENGTH: 1807
<212> TYPE: DNA
<213> ORGANISM: Agrobacterium tumefaciens

<400> SEQUENCE: 7

```
cgggatccat gtcatgaacc tctccttgat aaccagtgcg atcatctccc aaccaaaatg       60
gtggatctga caatggtcga taaggcggat gaattggacc gcagggtttc cgatgccttc      120
ttagaacgag aagcttctag gggaaggagg attactcaaa gctccaccga gtgcagcgct      180
gggttagctt gcaaaaggct ggccgatggt cgcttccccg agatctcagc tggtggaaag      240
gtagcagttc tctccgctta tatctatatt ggcaaagaaa ttctggggcg gatacttgaa      300
tcgaaacctt gggcgcgggc aacagtgagt ggtctcgttg ccatcgactt ggacaccatt      360
tgcatggatt ctccgaagc acaactaatc caagccctgt ttttgctgag cggtaaaaga      420
tgtgcaccga ttgatcttag tcatttcgtg gccatttcaa tctctaagac tgccggcttt      480
cgaaccctgc caatgccgct gtacgagaat ggcacgatga aatgcgttac cgggtttacc      540
ataacccttg aaggggccgt gccatttgac atggtagctt atggtcgaaa cctgatgctg      600 aagggtcgg caggttcctt tccaacaatc gacttgctct acgactgcag accgtttttt      660
gaccaatgtt ccgatagtgg acggatcggc ttctttccgg aggatgttcc taagccgaaa      720
gtggcggtca ttggcgctgg catttccgga ctcgtggtgg caaacgaact gcttcatgct      780
ggggtagacg atgttacaat atatgaagca agtgatcgtg ttggaggcaa gctttggtca      840
catgctttca gggacgctcc tagtgtcgtg gccgaaatgg gggcgatgcg atttcctcct      900
gctgcattct gcttgttttt cttcctcgag cgttacggcc tgtcttcgat gaggccgttc      960
ccaaatcccg gcacagtcga cacttacttg gtctaccaag gcgtccaata catgtggaaa     1020
gccgggcagc tgccaccgaa gctgttccat cgcgtttaca acggttggcg tgcgttcttg     1080
aaggacggtt tcatgagcg agatattgtg ttggcttcgc ctgtcgctat tactcaggcc     1140
ttgaaatcag gacacattag gtgggctcat gactcctggc aaatttggct gaaccgtttc     1200
gggagggagt ccttctcttc agggatagag aggatctttc tgggcacaca tcctcctggt     1260
ggtaaacatg gagttttcct catgattggg acctattcaa gctaatggga ataggatctg     1320
gcggggtttg gtccagtttt tgaaagcggg tttattgaga tcctccgctt ggtcatcaac     1380
ggatatgaag aaaatcagcg gatgtgccct gaaggaatct cagaacttcc acgtcggatc     1440
gcatctgaag tggttaacgg tgtgtctgtg agccagcgca tatgccatgt tcaagtcagg     1500
gcgattcaga aggaaaagac aaaaataaag ataaggctta agagcgggat atctgaactt     1560
tatgataagg tggtggtcac atctggactc gcaaatatcc aactcaggca ttgcctgaca     1620
```

```
tgcgatacca atattttca ggcaccagtg aaccaagcgg ttgataacag ccatatgaca    1680
ggatcgtcaa aactcttcct gatgactgaa cgaaaattct ggttagacca tatcctcccg    1740
tcttgtgtcc tcatggacgg gatcgcaaaa gcagtgtatt gcctggacta tgagtcgcag    1800
gatcccg                                                              1807

<210> SEQ ID NO 8
<211> LENGTH: 2
<212> TYPE: PRT
<213> ORGANISM: Agrobacterium tumefaciens

<400> SEQUENCE: 8

Met Ser
  1

<210> SEQ ID NO 9
<211> LENGTH: 2544
<212> TYPE: DNA
<213> ORGANISM: Agrobacterium tumefaciens

<400> SEQUENCE: 9
gaagatctga tcatggactg aatctaattt tcggtccaac ttgcacagga aagacgacga     60
ccgcgatagc tcttgcccag cagacagggc ttccagtcct ttcgcttgat cgggtccaat    120
gctgtcctca actatcaacc ggaagcggac gaccaacagt ggaagaactg aaaggaacga    180
cgcgtctcta ccttgatgat cggcctctgg tggagggtat catcgcagcc aagcaagctc    240
atcataggct gatcgaggag gtgtataatc atgaggccaa cggcgggctt attcttgagg    300
gaggatccat gtcatgaacc tctccttgat aaccagtgcg atcatctccc aaccaaaatg    360
gtggatctga caatggtcga taaggcggat gaattggacc gcagggtttc cgatgccttc    420
ttagaacgag aagcttctag gggaaggagg attactcaaa gctccaccga gtgcagcgct    480
gggttagctt gcaaaaggct ggccgatggt cgcttccccg agatctcagc tggtggaaag    540
gtagcagttc tctccgctta tatctatatt ggcaaagaaa ttctgggcg gatacttgaa    600 tcgaaccctt gggcgcgggc aacagtgagt ggtctcgttg ccatcgactt ggacaccatt    660
tgcatggatt tctccgaagc acaactaatc caagccctgt ttttgctgag cggtaaaaga    720
tgtgcaccga ttgatcttag tcatttcgtg gccatttcaa tctctaagac tgccggcttt    780
cgaaccctgc caatgccgct gtacgagaat ggcacgatga aatgcgttac cgggtttacc    840
ataacccttg aagggccgt gccatttgac atggtagctt atggtcgaaa cctgatgctg    900 aagggtcgg caggttcctt ccaacaatc gacttgctct acgactgcag accgtttttt    960
gaccaatgtt ccgatagtgg acggatcggc ttctttccgg aggatgttcc taagccgaaa   1020
gtggcggtca ttggcgctgg catttccgga ctcgtggtgg caaacgaact gcttcatgct   1080
ggggtagacg atgttacaat atatgaagca agtgatcgtg ttggaggcaa gctttggtca   1140
catgctttca gggacgctcc tagtgtcgtg gccgaaatgg gggcgatgcg atttcctcct   1200
gctgcattct gcttgttttt cttcctcgag cgttacggcc tgtcttcgat gaggccgttc   1260
ccaaatcccg gcacagtcga cacttacttg gtctaccaag gcgtccaata catgtggaaa   1320
gccgggcagc tgccaccgaa gctgttccat cgcgtttaca acggttggcg tgcgttcttg   1380
aaggacggtt tcatgagcg agatattgtg ttggcttcgc ctgtcgctat tactcaggcc   1440
ttgaaatcag gacacattag gtgggctcat gactcctggc aaatttggct gaaccgtttc   1500
gggagggagt ccttctcttc agggatagag aggatctttc tggcacaca tcctcctggt   1560
```

-continued

```
ggtaaacatg gagttttcct catgattggg acctattcaa gctaatggga ataggatctg   1620
gcggggtttg gtccagtttt tgaaagcggg tttattgaga tcctccgctt ggtcatcaac   1680
ggatatgaag aaaatcagcg gatgtgccct gaaggaatct cagaacttcc acgtcggatc   1740
gcatctgaag tggttaacgg tgtgtctgtg agccagcgca tatgccatgt tcaagtcagg   1800
gcgattcaga aggaaaagac aaaaataaag ataaggctta agagcgggat atctgaactt   1860
tatgataagg tggtggtcac atctggactc gcaaatatcc aactcaggca ttgcctgaca   1920
tgcgatacca atattttca ggcaccagtg aaccaagcgg ttgataacag ccatatgaca   1980
ggatcgtcaa aactcttcct gatgactgaa cgaaaattct ggttagacca tatcctcccg   2040
tcttgtgtcc tcatggacgg gatcgcaaaa gcagtgtatt gcctggacta tgagtcgcag   2100
gatccacctc gttgctcaac tgcatggcgc gaaacagcta ttggagtgca gatttttcgtt   2160 ggcatattat tcgccacaag ttacccgacc aagagacctt catgaaagcg gccaaggcca   2220
gagttaagca gatgttgcac cccgctgcag gccattctat tattcaagag ttggtttatc   2280
tttggaatga acctcggctg aggcccattc tgaaagagat cgatggatat cgatatgcca   2340
tgttgtttgc tagccagaac cagatcacgg cagatatgct attgcagctt gacgcaaata   2400
tggaaggtaa gttgattaat gggatcgctc aggagtattt catccatgcg cgccaacagg   2460
aacagaaatt cccccaagtt aacgcagccg ctttcgacgg attcgaaggt catccgttcg   2520
gaatgtatta gtgatcagat cttc                                          2544
```

<210> SEQ ID NO 10
<211> LENGTH: 2268
<212> TYPE: DNA
<213> ORGANISM: Agrobacterium tumefaciens

<400> SEQUENCE: 10

```
atgtcagctt cacctctcct tgataaccag tgcgatcatc tcccaaccaa aatggtggat     60
ctgacaatgg tcgataaggc ggatgaattg gaccgcaggg tttccgatgc cttcttagaa    120
cgagaagctt ctaggggaag gaggattact caaaagctcca ccgagtgcag cgctgggtta   180
gcttgcaaaa ggctggccga tggtcgcttc cccgagatct cagctggtgg aaaggtagca    240
gttctctccg cttatatcta tattggcaaa gaaattctgg ggcggatact tgaatcgaaa    300
ccttgggcgc gggcaacagt gagtggtctc gttgccatcg acttggacac catttgcatg    360
gatttctccg aagcacaact aatccaagcc ctgttttgc tgagcggtaa agatgtgca     420 ccgattgatc ttagtcattt cgtggccatt tcaatctcta agactgccgg ctttcgaacc    480
ctgccaatgc cgctgtacga gaatggcacg atgaaatgcg ttaccgggtt taccataacc    540
cttgaagggg ccgtgccatt tgacatggta gcttatggtc gaaacctgat gctgaagggt    600
tcggcaggtt cctttccaac aatcgacttg ctctacgact gcagaccgtt ttttgaccaa    660
tgttccgata gtggacggat cggcttcttt ccggaggatg ttcctaagcc gaaagtggcg    720
gtcattggcg ctggcatttc cggactcgtg tggcaaacg aactgcttca tgctgggggta   780 gacgatgtta caatatatga agcaagtgat cgtgttggag gcaagctttg gtcacatgct    840
ttcagggacg ctcctagtgt cgtggccgaa atggggggcga tgcgatttcc tcctgctgca    900
ttctgcttgt ttttcttcct cgagcgttac ggcctgtctt cgatgaggcc gttcccaaat    960
cccggcacag tcgacactta cttggtctac caaggcgtcc aatacatgtg gaaagccggg   1020
cagctgccac cgaagctgtt ccatcgcgtt tacaacggtt ggcgtgcgtt cttgaaggac   1080
```

-continued

```
ggttttcatg agcgagatat tgtgttggct tcgcctgtcg ctattactca ggccttgaaa    1140
tcaggacaca ttaggtgggc tcatgactcc tggcaaattt ggctgaaccg tttcgggagg    1200
gagtccttct cttcagggat agagaggatc tttctgggca cacatcctcc tggtggtaaa    1260
catggagttt tcctcatgat tgggacctat tcaagctaat gggaatagga tctggcgggg    1320
tttggtccag tttttgaaag cgggtttatt gagatcctcc gcttggtcat caacggatat    1380
gaagaaaatc agcggatgtg ccctgaagga atctcagaac ttccacgtcg gatcgcatct    1440
gaagtggtta acgtgtgtc tgtgagccag cgcatatgcc atgttcaagt cagggcgatt    1500
cagaaggaaa agacaaaaat aaagataagg cttaagagcg ggatatctga actttatgat    1560
aaggtggtgg tcacatctgg actcgcaaat atccaactca ggcattgcct gacatgcgat    1620
accaatattt ttcaggcacc agtgaaccaa gcggttgata acagccatat gacaggatcg    1680
tcaaaactct tcctgatgac tgaacgaaaa ttctggttag accatatcct cccgtcttgt    1740
gtcctcatgg acgggatcgc aaaagcagtg tattgcctgg actatgagtc gcaggatccg    1800
aatggtaaag gtctagtgct catcagttat acatgggagg acgactccca caagctgttg    1860
gcggtccccg acaaaaaaga gcgattatgt ctgctgcggg acgcaatttc gagatctttc    1920
ccggcgtttg cccagcacct atttcctgcc tgcgctgatt acgaccaaaa tgttattcaa    1980
catgattggc ttacagacga gaatgccggg ggagctttca aactcaaccg gcgtggtgag    2040
gatttttatt ctgaagaact tttctttcaa gcactggaca cggctaatga taccggagtt    2100
tacttggcgg gttgcagttg ttccttcaca gtggatggg tggagggtgc tattcagacc    2160
gcgtgtaacg ccgtctgtgc aattatccac aattgtggag gcattttggc aaagggcaat    2220
cctctcgaac actcttggaa gagatataac taccgcagta gaaattag              2268
```

<210> SEQ ID NO 11
<211> LENGTH: 1404
<212> TYPE: DNA
<213> ORGANISM: Agrobacterium tumefaciens

<400> SEQUENCE: 11

```
atggtggcca ttacctcgtt agcccaaagc ctagaacacc tgaaacggaa agactactcc     60
tgcttagaac tagtagaaac tctgatagcg cgttgtgaag ctgcaaaatc attaaacgcc    120
cttctggcta cagactggga tggtttgcgg cgaagcgcca aaaaaattga tcgccatgga    180
aacgccggag taggtctttg cggcattcca ctctgtttta aggcgaacat cgctaccggc    240
gtatttccca caagcgccgc tacgccggcg ctgataaacc acttgccaaa gataccatcc    300
cgcgtcgcag aaagactttt ttcagctgga gcactgccgg gtgcctcggg aaatatgcat    360
gagttatcgt ttggaattac aagcaacaac tatgccaccg gggcggtgcg aaaccctgtgg   420 aatccagatc tgataccagg gggctcaagc ggtggtgtgg ctgctgcggt agcaagccga    480
ttgatgttag gcggcatagg caccgatacc ggtgcatctg ttcgcctacc cgcagccctg    540
tgtggcgtag taggatttcg accgacgctt ggtagatatc cgggagatcg gataataccg    600
gttagcccta cccgggacac tcccggaatc atagcgcagt gcgtagccga tgttgtaatc    660
ctcgaccgga taatttccgg cacaccggag agaataccac ccgtgccgct gaagggggcta   720 aggatcggcc tccctacaac ctactttat gatgaccttg atgctgatgt ggccctagca    780
gctgaaacaa cgattcgcct gctagcaaac aaaggcgtaa cttttgttga agctaacatt    840
ccccaacttg acgaactgaa taaggggggcc agcttcccag ttgcactcta tgaatttcca    900
cacgctctaa aacagtatct cgacgacttt gtaaaaactg tttcttttc tgacgtcatc    960
```

-continued

```
aaaggaattc gtagccctga tgtagccaac attgccaatg cgcaaattga tggacatcaa    1020
atttccaaag ctgaatatga actggcccgc cactccttca gaccaagact tcaagccacc    1080
tatcgcaact acttcaaact gaatagatta gatgctattc tcttcccaac agcacccttg    1140
gtggccagac ccataggtca ggattcctca gttatccaca atggcacgat gctggacaca    1200
ttcaagatct acgtgcgaaa tgtggaccca agcagcaacg caggcctacc tggcttgagc    1260
attcctgttt gcctgacacc tgatcgcttg cctgttggaa tggagatcga tggattagcg    1320
gattcagacc aacgtctgtt agcaatcggg ggggcattgg aagaagccat tggattccga    1380
tattttgccg gtttacccaa ttaa                                            1404

<210> SEQ ID NO 12
<211> LENGTH: 723
<212> TYPE: DNA
<213> ORGANISM: Agrobacterium tumefaciens

<400> SEQUENCE: 12
atggacctgc atctaatttt cggtccaact tgcacaggaa agacgacgac cgcgatagct      60
cttgcccagc agacagggct tccagtcctt tcgcttgatc gggtccaatg ctgtcctcaa     120
ctatcaaccg gaagcggacg accaacagtg gaagaactga aaggaacgac gcgtctctac     180
cttgatgatc ggcctctggt ggagggtatc atcgcagcca agcaagctca tcataggctg     240
atcgaggagg tgtataatca tgaggccaac ggcgggctta ttcttgaggg aggatccacc     300
tcgttgctca actgcatggc gcgaaacagc tattggagtg cagattttcg ttggcatatt     360
attcgccaca agttacccga ccaagagacc ttcatgaaag cggccaaggc cagagttaag     420
cagatgttgc accccgctgc aggccattct attattcaag agttggttta tctttggaat     480
gaacctcggc tgaggcccat tctgaaagag atcgatggat atcgatatgc catgttgttt     540
gctagccaga accagatcac ggcagatatg ctattgcagc ttgacgcaaa tatggaaggt     600
aagttgatta atgggatcgc tcaggagtat ttcatccatg cgcgccaaca ggaacagaaa     660
ttcccccaag ttaacgcagc cgctttcgac ggattcgaag gtcatccgtt cggaatgtat     720
tag                                                                    723
```